United States Patent
Storer

(10) Patent No.: US 6,566,365 B1
(45) Date of Patent: May 20, 2003

(54) METHOD FOR THE TREATMENT OF FLAVIVIRIDEA VIRAL INFECTION USING NUCLEOSIDE ANALOGUES

(75) Inventor: Richard Storer, Baie d'Urfe (CA)

(73) Assignee: BioChem Pharma Inc. (CA)

( * ) Notice: Subject to any disclaimer, the term of this patent is extended or adjusted under 35 U.S.C. 154(b) by 0 days.

(21) Appl. No.: 09/704,832

(22) Filed: Nov. 3, 2000

Related U.S. Application Data

(60) Provisional application No. 60/163,405, filed on Nov. 4, 1999, and provisional application No. 60/163,394, filed on Nov. 4, 1999.

(51) Int. Cl.⁷ .................... A61K 31/52; A61K 31/53; A61K 31/415
(52) U.S. Cl. ............... 514/261; 514/262; 514/241; 514/245; 514/246; 514/385; 514/393
(58) Field of Search ................ 514/261, 262, 514/385, 393, 241, 245, 246

(56) References Cited

U.S. PATENT DOCUMENTS

| | | |
|---|---|---|
| 5,041,449 A | 8/1991 | Belleau et al. |
| 5,179,104 A | 1/1993 | Chu et al. |
| 5,270,315 A | 12/1993 | Belleau et al. |
| 5,276,151 A | 1/1994 | Liotta |
| 5,444,063 A | 8/1995 | Schinazi |
| 5,637,574 A | 6/1997 | Burns et al. |
| 5,684,010 A | 11/1997 | Schinazi |
| 5,767,122 A | 6/1998 | Chu et al. |
| 5,789,394 A * | 8/1998 | Nguyen-Ba et al. .......... 514/81 |
| 5,792,773 A | 8/1998 | Chu et al. |
| 5,817,667 A | 10/1998 | Chu et al. |
| 5,830,898 A | 11/1998 | Schinazi |
| 5,834,474 A | 11/1998 | Schinazi |
| 5,922,867 A | 7/1999 | Mansour et al. |
| 5,925,643 A | 7/1999 | Chu |
| 5,955,610 A | 9/1999 | Nguyen-Ba et al. |
| 6,069,250 A | 5/2000 | Mansour et al. |
| 6,069,252 A | 5/2000 | Liotta et al. |

FOREIGN PATENT DOCUMENTS

| | | |
|---|---|---|
| AU | 631 786 | 10/1989 |
| WO | WO92/10497 | 6/1992 |
| WO | WO92/18517 | 10/1992 |
| WO | WO92/20669 | 11/1992 |
| WO | WO95/07086 | 3/1995 |
| WO | WO96/07413 | 3/1996 |
| WO | WO97/21706 | 6/1997 |
| WO | WO98/20879 | 5/1998 |
| WO | WO00/47759 | 8/2000 |
| WO | WO00/57861 | 10/2000 |
| WO | WO01/06986 | 2/2001 |

OTHER PUBLICATIONS

Chen Huachun et al., "Pharmacokinetics of (–)-β-D-2-aminopurine Dioxolane and (–)-β-D-2-Amino-6-Chloropurine Dioxolane and Their Antiviral Metabolite (–)-β-D-Dioxolane Guanine in Rhesus Monkeys" Antimicrobial Agents and Chemotherapy, 40, 2332–2336 (1996).

Good, Steven S. et al., "Disposition in the Dog and the Rat of 2,6-Diamino-9-(2-Hydroxyethoxymethy)Purine(A134U), a Potential Prodrug of Acyclovir" The Journal of Pharmacology and Experimental Therapeutics 227, 644–651, USA.

Gu, Z. et al. "Mechanism of Action and in Vitro Activity, of 1',3'-Dioxolanylpurine Nucleoside Analogues against Sensitive and Drug–Resistant Human Immunodeficiency Virus Type 1 Variants," Antimicrobial Agents and Chemotherapy, 43, 2376–2382 (1999).

Kim, H.O., et al., "Asymmetric Synthesis of 1,3-Dioxolane-Pyrimidine Nucleosides and Their Anti-HIV Activity," Journal of Medicinal Chemistry, 1992, vol. 35, No. 11, pp. 1987–1992.

Kim, Hea O., et al., 1,3-Dioxolanylpurine Nucleosides (2R,4R) and 2R,4S) with Selective Anti-HIV-1 Activity in Human Lymphocytes Journal of Medicinal Chemistry 36, 30–37.

(List continued on next page.)

Primary Examiner—Sreeni Padmanabhan
Assistant Examiner—Shaojia A. Jiang
(74) Attorney, Agent, or Firm—Millen, White, Zelano & Branigan, P.C.

(57) ABSTRACT

In accordance with the present invention there is provided a method for treating or preventing a Flaviviridea viral infection in a host comprising administering a therapeutically effective amount of at least one compound of formula (I) or (II)

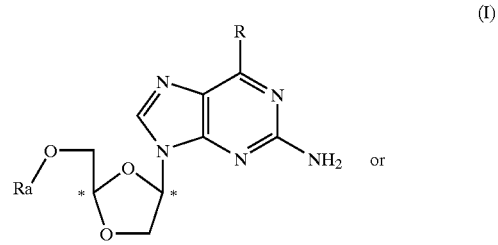

(I)

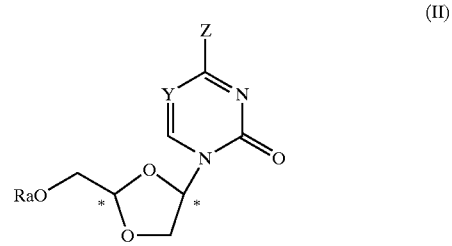

(II)

or a pharmaceutically acceptable salts thereof, wherein Ra, R, Z and Y are defined in the application.

66 Claims, No Drawings

OTHER PUBLICATIONS

Kim, Hea O. et al. "L–β–(2S,4S)–and L– –(2S,4R)–Dioxolanyl Nucleosides as Potential Anti–HIV Agents: Asymmetric Synthesis and Structure–Activity Relationships" Journal of Medicinal Chemistry 36, 519–528.

Kim, Hea O. et al. Potent Anti–HIV and Anti–HBV Activities of (–)–L–β–Dioxolane–C and (+)–L–β–Dioxolane–T and Their Asymmetric Syntheses. Tetrahedron Letters, vol. 33, No. 46, pp. 6899–6902, 1992.

Norbeck, Daniel W. et al. "(+)–1–[(2β, 4β)–2–(Hydroxymethyl)–4–dioxolanyl]thymine) A new 2',3'–Dideoxynucleoside Prototype with In Vitro Activity Against HIV" Tetrahedron Letters, 30, 6263–6266 (1989).

Schinazi, R.F. et al., "Developments of (–)–β–D–2,6–Diaminopurine Dioxolane as a Potential Antiviral Agent," Antiviral Research, vol. 23, Supplement 1 (1994).

Spector, Thomas et al. "Conversion of 2,3–Diamino–9–(2–Hydroxyethoxymethyl) Purine to Acyclovir as Catalyzed by Adenosine Deaminase" Biochemical Pharmacology vol. 32, No. 17, pp. 2505–2509, 1983 Great Britain.

Triangle Pharmaceuticals, website, "DAPD: A Potential Antiviral Purine Nucleoside Analogue," site last updated on Feb. 5, 1999.

Eng–Chun Mar et al. "Some nucleoside analogs with anti–human immunodeficiency virus activity inhibit replication of Epstein–Bar virusus," Antiviral Research 28, (1995) 1–11.

Weitman, Steve et al. "The New Dioxolane (–)–2'–Deoxy–3'–oxacytidine (BCH–4556, Troxacitabine), Has Activity Against Pancreatic Human Tumor Xenografts," Clinical Cancer Research, vol. 6, 1574–1578, Apr. 2000.

Rabbani, Shafaat A. et al., "Effect of Nucleoside Analogue BCH–4556 on Prostate Cancer Growth and Metastases In Vitro and In Vivo" Cancer Research 58, pp. 3461–3465, Aug. 1, 1998.

Schwartz, P.M. et al. "β–L1,3–Dioxolane–Cytidine: A Novel Nucleoside That Inhibits Proliferation and Induces Differentiation of Keratinocytes in vitro," Skin Physiol 1998, 11:207–213.

Grove, K.L. et al., β–L–(–)–Dioxolane Cytidine (β–L–(–)–OddC) As A Potent Compound For The Treatment of Cancer, Nucleosides & Nucleotides, 16(7–9), 1229–1233 (1997).

Kadhim, Salam A. et al., "Potent Antitumor Activity of a Novel Nucleoside Analogue, BCH–4556 (β–L–Dioxolane–cytidine), in Human Renal Cell Carcinoma Xenograft Tumor Models," Cancer Research 57, 4803–4810, Nov. 1, 1997.

Grove, Kristie L. and Yung–Chi Cheng, "Uptake and Metabolism of the New Anticancer Compound β–L–(–)–Dioxolane–Cytidine in Human Prostate Carcinoma DU–145 Cells," Cancer Research 56, 4187–4191, Sep. 15, 1996.

Lee, Migyoung et al. "Dioxolane Cytosine Nucleosides as Anti–hepatitis B Agents,"Bioorganic & Medicinal Chemistry Letters, vol. 5, No. 17, pp. 2011–2014, 1995.

Grove, Kristie L. et al. "Anticancer Activity Activity of β–L–(–)–Dioxolane–Cytidine, a Novel Nucleoside Analogue with the Unnatural L Configuration," Cancer Research 55, 3008–30111, Jul. 15, 1995.

Mansour, Tarek S. et al., "Structure–Activity Relationships Among a New Class of Antiviral Heterosubstituted 2',3'–Dideoxynucleoside Analogues," Nucleosides & Nucleotides, 14(3–5), 627–635 (1995).

Siu, L.L. et al. "Activity of (–)–2'–deoxy–3'–oxacytidine (BCH–4556) against human tumor colony–forming units," Annals of Oncology 9:885–891, 1998.

Moore, Laura E. et al., "Preclinical pharmacokinetics of L–dioxolane–cytidine, a novel anticancer agent in rats," Cancer Chemother Pharmacol. (1997) 39:532–536.

* cited by examiner

METHOD FOR THE TREATMENT OF FLAVIVIRIDEA VIRAL INFECTION USING NUCLEOSIDE ANALOGUES

This application claims priority from Serial No. Application 60/163,405 and Serial No. Application 60/163,394 filed Nov. 4 1999 which are herein incorporated by reference.

FIELD OF THE INVENTION

The present invention relates to a method for the treatment or prevention Flaviviridae viral infection using nucleoside analogues.

BACKGROUND OF THE INVENTION

Hepatitis is a disease occurring throughout the world. It is generally of viral nature, although there are other causes known. Viral hepatitis is by far the most common form of hepatitis. Nearly 750,000 Americans are affected by hepatitis each year, and out of those, more than 150,000 are infected with the hepatitis C virus (HCV).

HCV is a positive-stranded RNA virus belonging to the Flaviviridae family and has closest relationship to the pestiviruses that include hog cholera virus and bovine viral diarrhea virus (BVDV). HCV is believed to replicate through the production of a complementary negative-strand RNA template. Due to the lack of efficient culture replication system for the virus, HCV particles were isolated from pooled human plasma and shown, by electron microscopy, to have a diameter of about 50–60 nm. The HCV genome is a single-stranded, positive-sense RNA of about 9,600 bp coding 30 for a polyprotein of 3009–3030 amino-acids, which is cleaved, post-translationally by cellular and two viral proteinases into mature viral proteins (core, E1, E2, p7, NS2, NS3, NS4A, NS4B, NS5A, NS5B). It is believed that the structural proteins, E1 and E2, the major glycoproteins are embedded into a viral lipid envelop and form stable heterodimers. The structural core protein interacts with the viral RNA genome to form the nucleocapsid. The genes or regions designated NS2 to NS5 code for nonstructural proteins some of which have enzymatic functions involved in virus replication and protein processing including a polymerase, protease and helicase.

The main sources of contamination with HCV is blood. The magnitude of the HCV infection as a health problem is illustrated by the prevalence among high-risk groups. For example, 60% to 90% of hemophiliacs and more than 80% of intravenous drug abusers in western countries are chronically infected with HCV. For intravenous drug abusers, the prevalence varies from about 28% to 70% depending on the population studied. The proportion of new HCV infections associated with post-transfusion has been markedly reduced lately due to advances in diagnostic tools used to screen blood donors.

The treatment currently available for HCV infection is interferon (IFN), ribavirin, and a combinaison of the two (REBETRON). However, according to different clinical studies, only 70% of treated patients normalize alanine aminotransferase (ALT) levels in the serum and after discontinuation of IFN, 35% to 45% of these responders relapse. In general, only 20% to 25% of patients have long-term responses to IFN. On the other hand, pilot studies suggest that combination treatment with IFN plus Ribavirin (RIBA) results in sustained response in the majority of patients. Different genotypes of HCV respond differently to IFN therapy, genotype 1b is more resistant to IFN therapy than type 2 and 3.

There is therefore a great need for the development of therapeutic agent for treating or preventing Flaviviridae viral infection.

SUMMARY OF THE INVENTION

The present invention provides a method for treating or preventing a Flaviviridea viral infection in a host comprising administering a therapeutically effective amount of at least one compound selected from:

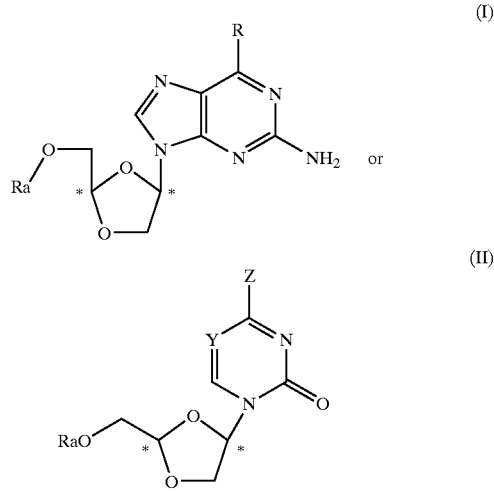

or a pharmaceutically acceptable salts thereof, wherein:
  R is H, —$NR_2R_3$ or $OR_4$ wherein
    $R_2$ is H, $C_{1-6}$ alkyl, $C_{2-6}$ alkenyl, $C_{2-6}$ alkynyl, $C_{3-8}$cycloalkyl;
    $R_3$ is H, $C_{1-6}$ alkyl, $C_{2-6}$ alkenyl, $C_{2-6}$ alkynyl;
    $R_4$ is H, $C_{1-6}$ alkyl, $C_{2-6}$ alkenyl, $C_{2-6}$ alkynyl; and
  Z is H, $OR_{4'}$, or —$NR_{2'}R_{3'}$ wherein:
    $R_{2'}$ is H, $C_{1-6}$ alkyl, $C_{2-6}$ alkenyl, $C_{2-6}$ alkynyl, $C_{3-8}$cycloalkyl,
    $R_{3'}$ is H, $C_{1-6}$ alkyl, $C_{2-6}$ alkenyl, or $C_{2-6}$ alkynyl;
    $R_{4'}$ is H, $C_{1-6}$ alkyl, $C_{2-6}$ alkenyl, $C_{2-6}$ alkynyl; and and;
  Y is N or C—X;
  X is chosen from of H, halogen, $C_{1-6}$ alkyl, $C_{2-6}$ alkenyl, $C_{2-6}$ alkynyl, CN, $CF_3$, $N_3$, $NO_2$, $C_{6-10}$ aryl, $C_{6-10}$ heteroaryl and CORb wherein Rb is chosen from of H, OH, SH, $C_{1-6}$ alkyl, $C_{1-6}$ aminoalkyl, $C_{1-6}$ alkoxy and $C_{1-6}$ thioalkyl;
  and Ra is chosen from of H, monophosphate, diphosphate, triphosphate, carbonyl substituted with a $C_{1-6}$ alkyl, $C_{2-6}$ alkenyl, $C_{2-6}$ alkynyl, $C_{6-10}$ aryl, and

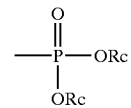

wherein each Rc are independently chosen from H, $C_{1-6}$ alkyl, $C_{2-6}$ alkenyl, $C_{2-6}$ alkynyl and an hydroxy protecting group,
wherein said nucleoside is present in the form of the (−) enantiomer, the (+) enantiomer or mixtures thereof, including racemic mixtures.

The present invention provides a method for treating a Flaviviridea viral infection in a host comprising administering a therapeutically effective amount of at least one compound as described in the present application.

The present invention provides a method for preventing a Flaviviridea viral infection in a host comprising administering a therapeutically effective amount of at least one compound as described in the present application.

The present invention provides a method for reducing the biological activity of a Flaviviridea viral infection in a host comprising administering a therapeutically effective amount of at least one compound as described in the present application.

In another aspect, there is provided a pharmaceutical formulation comprising the compound of the invention in combination with a pharmaceutically acceptable carrier or excipient.

Still another aspect, there is provided a method for treating or preventing a Flaviviridea viral infection in a host comprising administering to the subject a combination comprising at least one compound according to formula I or formula II and at least one further therapeutic agent.

In another aspect of the invention is the use of a compound according to formula I, for the preparation of a medicament for treating or preventing a viral infections in a host.

In another aspect of the invention is the use of a compound according to formula II, for the preparation of a medicament for treating or preventing a viral infection in a host.

DETAILED DESCRIPTION OF THE INVENTION

In one embodiment, the viral infection is chosen from Flaviviridea viral infections.

In one embodiment, the Flaviviridea viral infection is chosen from of Hepatitis C virus(HCV), bovine viral diarrhea virus(BVDV), hog cholera and yellow fever.

In an other embodiment, the Flaviviridea viral infection is Hepatitis C.

In one embodiment, there is also provided a method for inhibiting or reducing the activity of viral polymerase in a host, when compared to a standard comprising administering a therapeutically effective amount of a compound having the formula I.

In one embodiment, there is also provided a method for inhibiting or reducing the activity of viral polymerase in a host, when compared to a standard, comprising administering a therapeutically effective amount of a compound having the formula II.

In one embodiment, there is also provided a method for inhibiting the activity of viral polymerase in a host, when compared to a standard comprising administering a therapeutically effective amount of a compound having the formula I.

In one embodiment, there is also provided a method for inhibiting the activity of viral polymerase in a host, when compared to a standard, comprising administering a therapeutically effective amount of a compound having the formula II.

In one embodiment, there is also provided a method for reducing the activity of viral polymerase in a host, when compared to a standard comprising administering a therapeutically effective amount of a compound having the formula I.

In one embodiment, there is also provided a method for reducing the activity of viral polymerase in a host, when compared to a standard, comprising administering a therapeutically effective amount of a compound having the formula II.

In another embodiment, the viral polymerase is HCV polymerase.

In one embodiment, the compounds and methods of the present invention comprise those wherein the following embodiments are present, either independently or in combination.

In one embodiment, $R_4$ is $C_{1-6}$alkyl.

In one embodiment, $R_4$ is methyl or ethyl.

In one embodiment, R is $NH_2$, H or OH.

In a further embodiment R is $NH_2$ or OH.

In a further embodiment R is OH.

In one embodiment R is $-NR_2R_3$ wherein $R_2$ is $C_{3-8}$cycloalkyl and $R_3$ is H.

In one embodiment R is $-NR_2R_3$ wherein $R_2$ is $C_{3-5}$cycloalkyl and $R_3$ is H.

In one embodiment R is $-NR_2R_3$ wherein $R_2$ is cyclopropyl or cyclopentyl and $R_3$ is H.

In one embodiment R is $-NR_2R_3$ wherein $R_2$ is cyclopropyl and $R_3$ is H.

In one embodiment Ra is chosen from H, monophosphate, diphosphate, and triphosphate.

In one embodiment Ra is chosen from monophosphate, diphosphate, and triphosphate.

In one embodiment Ra is triphosphate.

In one embodiment Ra is H.

In one embodiment, Z is H, OH, $-NR_{2'}R_{3'}$ wherein:

$R_{2'}$ is H, or $C_{1-6}$ alkyl; and $R_{3'}$ is H, or $C_{1-6}$ alkyl.

In one embodiment, $R_{4'}$ is $C_{1-6}$alkyl.

In one embodiment, $R_{4'}$ is methyl or ethyl.

In one embodiment Z is chosen from OH or $NH_2$.

In one embodiment Z is OH.

In another embodiment Z is $NH_2$.

In another embodiment, Y is N.

In another embodiment, Y is C—X.

In another embodiment, X is H, $C_{1-6}$alkyl or halogen.

In another embodiment, X is H, methyl or halogen.

In another embodiment, X is methyl, $-HC=CH_2$ and $-C\equiv CH$.

In another embodiment, X is H or halogen.

In another embodiment, X is halogen.

In another embodiment, X is H, methyl or F.

In another embodiment, X is H or F.

In another embodiment, X is H.

In another embodiment, X is F.

It will be appreciated by those skilled in the art that the compounds of formula (I) contain at least two chiral centers which are marked by an asterisk (*) on the general formula (I) or (II) The compounds of formula (I) and (II) thus exist in the form of two different optical isomers (i.e. (+) or (−) enantiomers or β-L and β-D). All such enantiomers and mixtures thereof including racemic mixtures are included within the scope of the invention.

The single optical isomer or enantiomer can be obtained by method well known in the art, such as chiral synthesis, chiral HPLC, enzymatic resolution and chiral auxiliary.

Compounds of the invention include, for compounds having the structure of the formula I:

Compound 1 cis-2-hydroxymethyl-4-(2'-amino-6'-cyclopropylamino-purine-9'-yl)-1,3-dioxolane; Compound 1(−) (−)cis-2-hydroxymethyl-4-(2'-amino-6'-cyclopropylamino-purine-9'-yl)-1,3-dioxolane; Compound 1(+) (+)cis-2-hydroxymethyl-4-(2'-amino-6'-cyclopropylamino-purine-9'-yl)-1,3-dioxolane

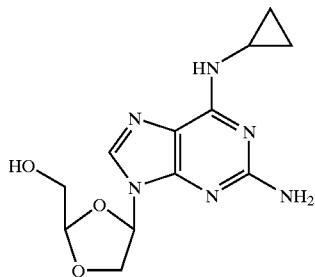

Compound 2 cis-2-hydroxymethyl-4-(2'-amino-6'-cyclobutylamino-purine-9'-yl)-1,3-dioxolane; Compound 2(−) (−)cis-2-hydroxymethyl-4-(2'-amino-6'-cyclobutylamino-purine-9'-yl)-1,3-dioxolane Compound 2(+) (+)cis-2-hydroxymethyl-4-(2'-amino-6'-cyclobutylamino-purine-9'-yl)-1,3-dioxolane

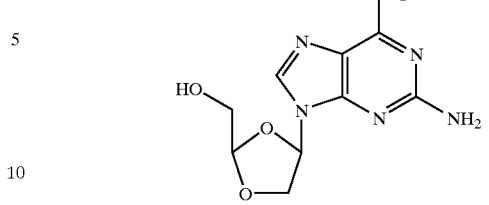

Compound 5 cis-2-hydroxymethyl-4-(guanin-9'-yl)-1,3-dioxolane; Compound 5(−) (−)-cis-2-hydroxymethyl-4-(guanin-9'-yl)-1,3-dioxolane; Compound 5(+) (+)-cis-2-hydroxymethyl-4-(guanin-9'-yl)-1,3-dioxolane

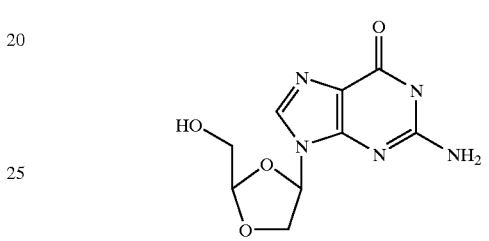

Compound 6 cis-2-hydroxymethyl-4-(adenin-9'-yl)-1,3-dioxolane; Compound 6(−) (−)-cis-2-hydroxymethyl-4-(adenin-9'-yl)-1,3-dioxolane; Compound 6(+) (+)-cis-2-hydroxymethyl-4-(adenin-9'-yl)-1,3-dioxolane

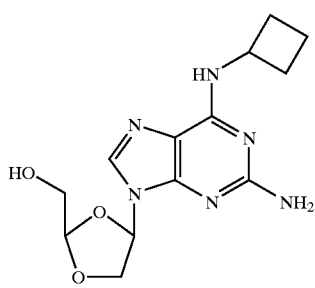

Compound 3 cis-2-hydroxymethyl-4-(2'-amino-6'-cyclopentylamino-purine-9'-yl)-1,3-dioxolane; Compound 3(−) (−)cis-2-hydroxymethyl-4-(2'-amino-6'-cyclopentylamino-purine-9'-yl)-1,3-dioxolane; Compound 3(+) (+)cis-2-hydroxymethyl-4-(2'-amino-6'-cyclopentylamino-purine-9'-yl)-1,3-dioxolane

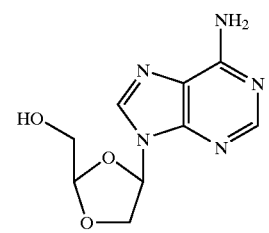

Compound 7 cis-2-hydroxymethyl-4-(2'amino-6'-chloro-purin-9'-yl)-1,3-dioxolane; Compound 7(−) (−)-cis-2-hydroxymethyl-4-(2'amino-6'-chloro-purin-9'-yl)-1,3-dioxolane; Compound 7(+) (+)-cis-2-hydroxymethyl-4-(2'amino-6'-chloro-purin-9'-yl)-1,3-dioxolane

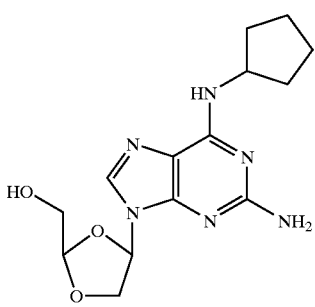

Compound 4-cis-2-hydroxymethyl-4-(2'-6'-diamino-purin-9'-yl)-1,3-dioxolane; Compound 4(−) (−)-cis-2-hydroxymethyl-4-(2'-6'-diamino-purin-9'-yl)-1,3-dioxolane; Compound 4(+) (+)-cis-2-hydroxymethyl-4-(2'-6'-diamino-purin-9'-yl)-1,3-dioxolane

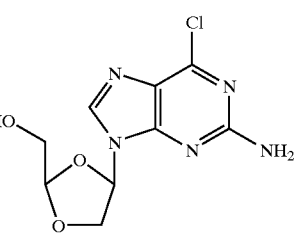

Compound 8 cis-2-hydroxymethyl-4-(2'amino-purin-9'-yl)-1,3-dioxolane; Compound 8(−) (−)-cis-2-hydroxymethyl-4-(2'amino-purin-9'-yl)-1,3-dioxolane; Compound 8(+) (+)-cis-2-hydroxymethyl-4-(2'amino-purin-9'-yl)-1,3-dioxolane

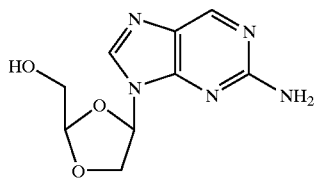

In a further aspect of the present invention compounds of the invention include

Compound 1(−) (−)-cis-2-hydroxymethyl-4-(2'-amino-6'-cyclopropylamino-purine-9'-yl)-1,3-dioxolane

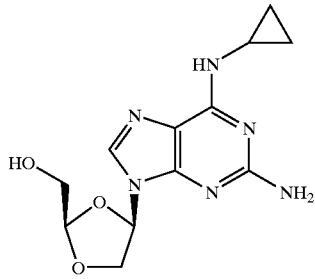

Compound 2(−) (−)-cis-2-hydroxymethyl-4-(2'-amino-6'-cyclobutylamino-purine-9'-yl)-1,3-dioxolane

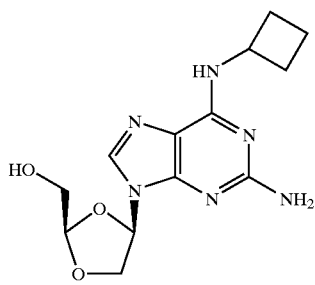

Compound 3(−) (−)-cis-2-hydroxymethyl-4-(2'-amino-6'-cyclopentylamino-purine-9'-yl)-1,3-dioxolane

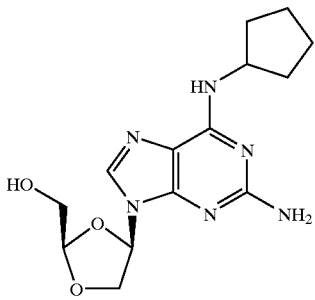

Compound 4(−) (−)-cis-2-hydroxymethyl-4-(2'-6'-diamino-purin-9'-yl)-1,3-dioxolane

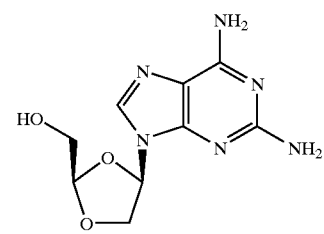

Compound 5(−) (−)-cis-2-hydroxymethyl-4-(guanin-9'-yl)-1,3-dioxolane

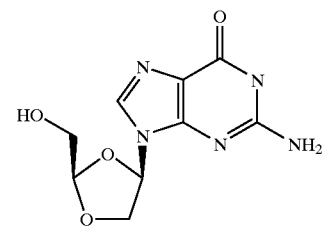

Compound 6(−) (−)-cis-2-hydroxymethyl-4-(adenin-9'-yl)-1,3-dioxolane

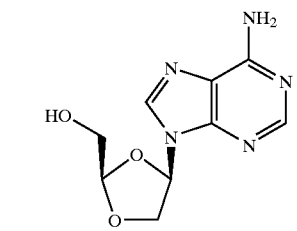

Compound 7(−) (−)-cis-2-hydroxymethyl-4-(2'amino-6'-chloro-purin-9'-yl)-1,3-dioxolane

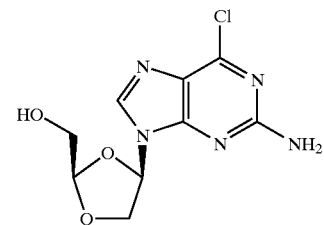

Compound 8(−) (−)cis-2-hydroxymethyl-4-(2'amino-purin-9'-yl)-1,3-dioxolane

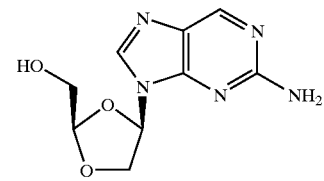

In a further embodiment, the compounds of the present invention have a triphosphate group in the 5' position. In a further aspect of the present invention, the compounds of formula (I) are represented by:

Compound 9 triphosphatecis-2-hydroxymethyl-4-(2'-amino-6'-cyclopropylamino-purine-9'-yl)-1,3-dioxolane; Compound 9(−) (−)-triphosphate-cis-2-hydroxymethyl-4-(2'-amino-6'-cyclopropylamino-purine-9'-yl)-1,3-dioxolane; Compound 9(+) (+)-triphosphate-cis-2-hydroxymethyl-4-(2'-amino-6'-cyclopropylamino-purine-9'-yl)-1,3-dioxolane

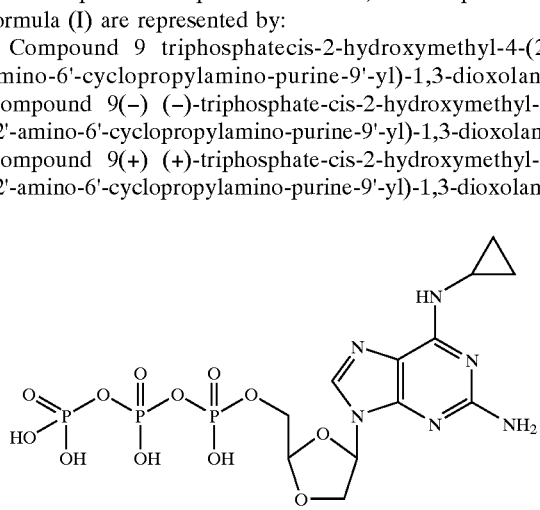

Compound 10 Triphosphate-cis-2-hydroxymethyl-4-(2'-amino-6'-cyclobutylamino-purine-9'-yl)-1,3-dioxolane; Compound 10(−) (−)-triphosphate-cis-2-hydroxymethyl-4-(2'-amino-6'-cyclobutylamino-purine-9'-yl)-1,3-dioxolane Compound 10(+) (+)-triphosphate-cis-2-hydroxymethyl-4-(2'-amino-6'-cyclobutylamino-purine-9'-yl)-1,3-dioxolane

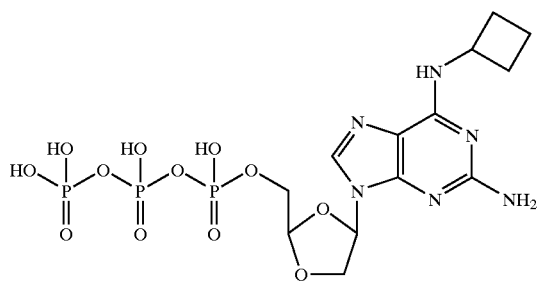

Compound 11 Triphosphate cis-2-hydroxymethyl-4-(2'-amino-6'-cyclopentylamino-purine-9'-yl)-1,3-dioxolane; Compound 11(−) (−)-triphosphate-cis-2-hydroxymethyl-4-(2'-amino-6'-cyclopentylamino-purine-9'-yl)-1,3-dioxolane; Compound 11(+) (+)-triphosphate-cis-2-hydroxymethyl-4-(2'-amino-6'-cyclopentylamino-purine-9'-yl)-1,3-dioxolane

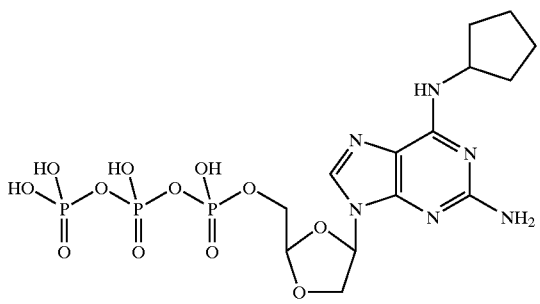

Compound 12 Triphosphate cis-2-hydroxymethyl-4-(2'-6'-diamino-purin-9'-yl)-1,3-dioxolane; Compound 12(−) (−)-triphosphate-cis-2-hydroxymethyl-4-(2'-6'-diamino-purin-9'-yl)-1,3-dioxolane; Compound 12(+) (+)-triphosphate-cis-2-hydroxymethyl-4-(2'-6'-diamino-purin-9'-yl)-1,3-dioxolane

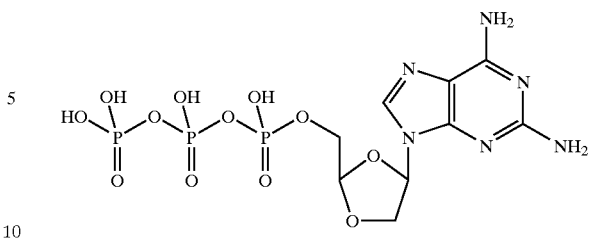

Compound 135 Triphosphate cis-2-hydroxymethyl-4-(guanin-9'-yl)-1,3-dioxolane; Compound 135(−) (−)-triphosphate-cis-2-hydroxymethyl-4-(guanin-9'-yl)-1,3-dioxolane; Compound 13(+) (+)-triphosphate-cis-2-hydroxymethyl-4-(guanin-9'-yl)-1,3-dioxolane

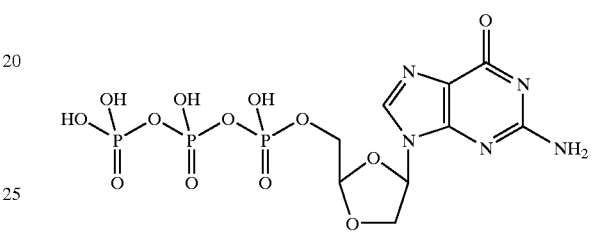

Compound 14 Triphosphate-cis-2-hydroxymethyl-4-(adenin-9'-yl)-1,3-dioxolane; Compound 14(−) (−)-triphosphate-cis-2-hydroxymethyl-4-(adenin-9'-yl)-1,3-dioxolane; Compound 14(+) (+)-triphosphate-cis-2-hydroxymethyl-4-(adenin-9'-yl)-1,3-dioxolane

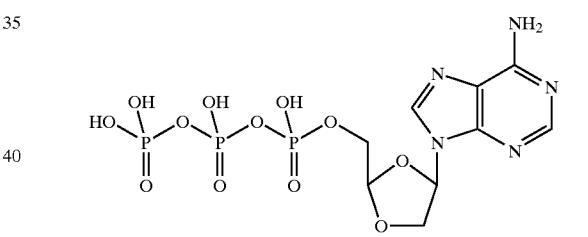

Compound 15 Triphosphate-cis-2-hydroxymethyl-4-(2'amino-6'-chloro-purin-9'-yl)-1,3-dioxolane; Compound 15(−) (−)-triphosphate-cis-2-hydroxymethyl-4-(2'amino-6'-chloro-purin-9'-yl)-1,3-dioxolane; Compound 15(+) (+)-triphosphate-cis-2-hydroxymethyl-4-(2'amino-6'-chloro-purin-9'-yl)-1,3-dioxolane

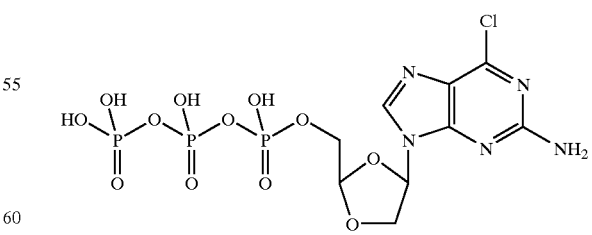

Compound 16 Triphosphate-cis-2-hydroxymethyl-4-(2'amino-purin-9'-yl)-1,3-dioxolane; Compound 16(−) (−)-triphosphate-cis-2-hydroxymethyl-4-(2'amino-purin-9'-yl)-1,3-dioxolane; Compound 16(+) (+)-triphosphate-cis-2-hydroxymethyl-4-(2'amino-purin-9'-yl)-1,3-dioxolane

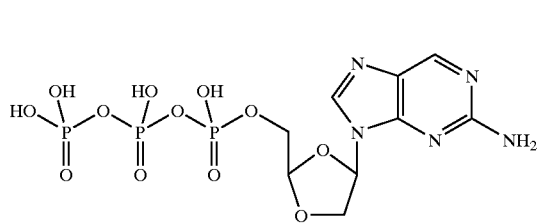

In a further aspect of the present invention compounds of the invention include:

Compound 9(−) (−)-triphosphate-cis-2-hydroxymethyl-4-(2'-amino-6'-cyclopropylamino-purine-9'-yl)-1,3-dioxolane

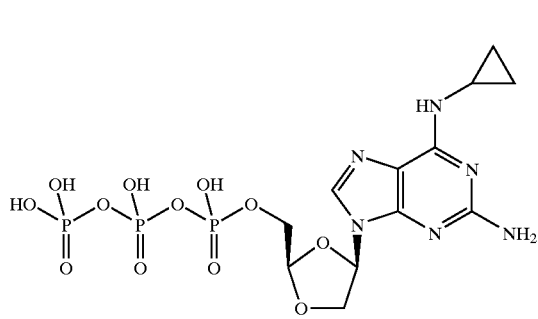

Compound 10(−) (−)-triphosphate-cis-2-hydroxymethyl-4-(2'-amino-6'-cyclobutylamino-purine-9'-yl)-1,3-dioxolane

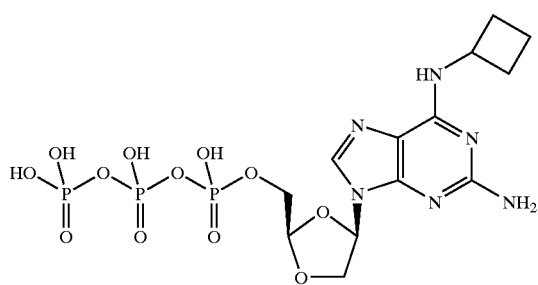

Compound 11(−) (−)-triphosphate-cis-2-hydroxymethyl-4-(2'-amino-6'-cyclopentylamino-purine-9'-yl)-1,3-dioxolane

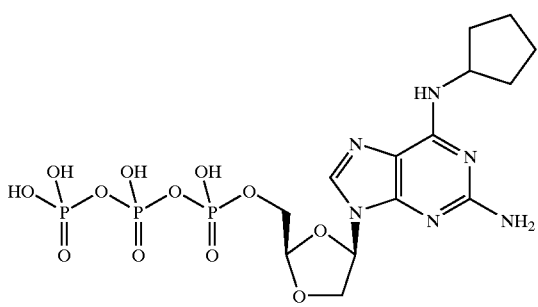

Compound 12(−) (−)-triphosphate-cis-2-hydroxymethyl-4-(2'-6'-diamino-purin-9'-yl)-1,3-dioxolane

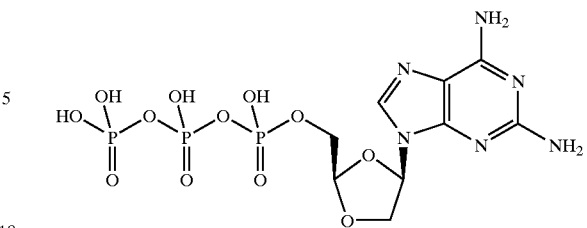

Compound 13(−) (−)-triphosphate-cis-2-hydroxymethyl-4-(guanin-9'-yl)-1,3-dioxolane

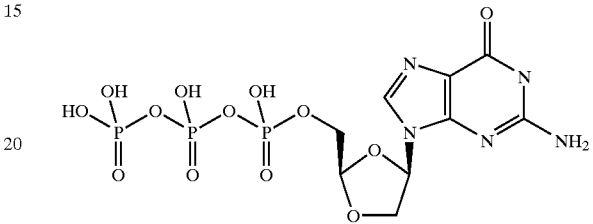

Compound 14(−) (−)-triphosphate-cis-2-hydroxymethyl-4-(adenin-9'-yl)-1,3-dioxolane

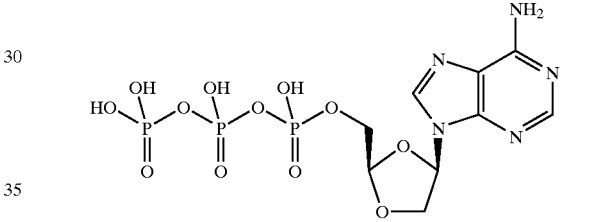

Compound 15(−) (−)-triphosphate-cis-2-hydroxymethyl-4-(2'amino-6'-chloro-purin-9'-yl)-1,3-dioxolane

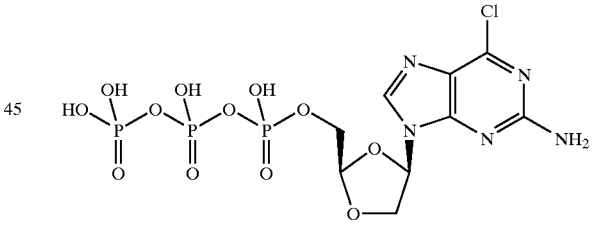

Compound 16(−) (−)-triphosphate cis-2-hydroxymethyl-4-(2'amino-purin-9'-yl)-1,3-dioxolane

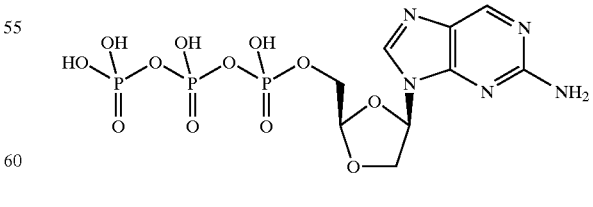

In a further embodiment of the present invention the compounds of formula (II) include:

In one embodiment, a compound of formula II is cis-2-hydroxymethyl-4-(cytosin-1'-yl)-1,3-dioxolane (compound#17)

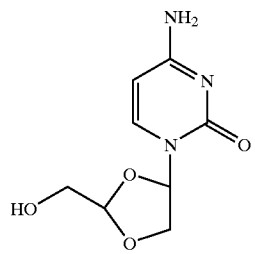

In one embodiment, a compound of formula II is (−)-cis-2-hydroxymethyl-4-(cytosin-1'-yl)-1,3-dioxolane (β-L-OddC) (compound#17 (−)).

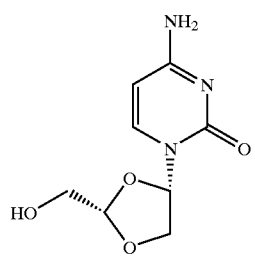

In one embodiment, a compound of formula II is (+)-cis-2-hydroxymethyl-4-(cytosin-1'-yl)-1,3-dioxolane (β-D-OddC) (compound#17 (+)).

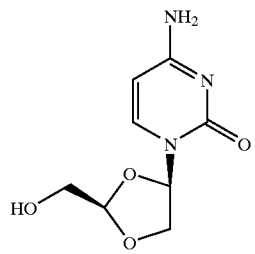

In another embodiment, a compound of formula II is cis-2-hydroxymethyl-4-(5'-fluorocytosin-1'-yl)-1,3-dioxolane(5FOddC) (compound#18).

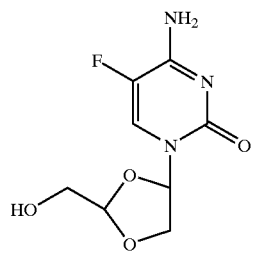

In another embodiment, a compound of formula II is (−)-cis-2-hydroxymethyl-4-(5'-fluorocytosin-1'-yl)-1,3-dioxolane(β-L-5FOddC) (compound#18 (−)).

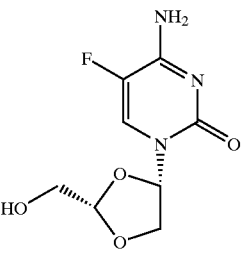

In another embodiment, a compound of formula II is (+)-cis-2-hydroxymethyl-4-(5'-fluorocytosin-1'-yl)-1,3-dioxolane(β-D-5FOddC) (compound#18 (+)).

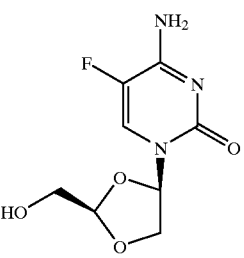

In another embodiment, a compound of formula II is cis-2-hydroxymethyl-4-(5'-azacytosin-1'-yl)-1,3-dioxolane (compound#19).

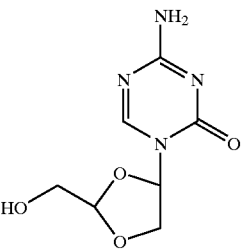

In another embodiment, a compound of formula II is (−)-cis-2-hydroxymethyl-4-(5'-azacytosin-1'-yl)-1,3-dioxolane (compound#19 (−)).

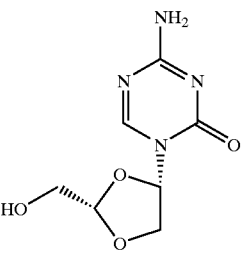

In another embodiment, a compound of formula II is (+)-cis-2-hydroxymethyl-4-(5'-azacytosin-1'-yl)-1,3-dioxolane(compound#19 (+)).

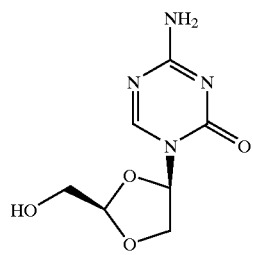

In another embodiment, a compound of formula II is cis-2-hydroxymethyl-4-(5'-methylcytosin-1'-yl)-1,3-dioxolane(compound#20).

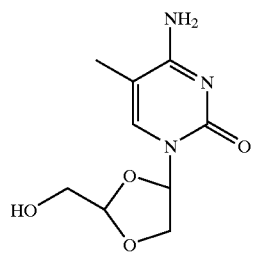

In another embodiment, a compound of formula II is (−)-cis-2-hydroxymethyl-4-(5'-methylcytosin-1'-yl)-1,3-dioxolan (compound#20 (−)).

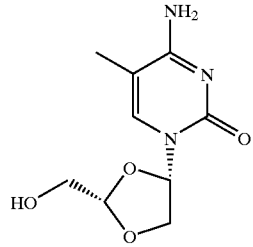

In another embodiment, a compound of formula II is (+)-cis-2-hydroxymethyl-4-(5'-methylcytosin-1'-yl)-1,3-dioxolane (compound#20 (+)).

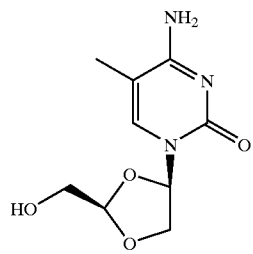

In another embodiment, a compound of formula II is cis-2-hydroxymethyl-4-(N-1'-thyminyl)-1,3-dioxolane (compound#21).

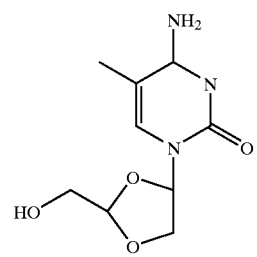

In another embodiment, a compound of formula II is (−)-cis-2-hydroxymethyl-4-(N-1'-thyminyl)-1,3-dioxolane (compound#21 (−)).

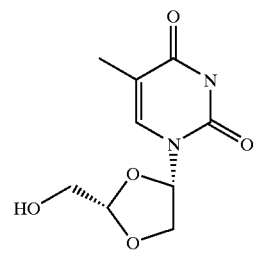

In another embodiment, a compound of formula II is (+)-cis-2-hydroxymethyl-4-(N-1'-thyminyl)-1,3-dioxolane (compound#21 (+)).

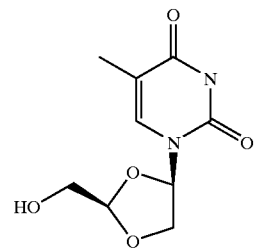

In a further embodiment, the compounds of the present invention have a triphosphate group in the 5' position. In a further aspect of the present invention, the compounds of formula (II) are represented by:

In one embodiment, a compound of formula II is triphosphate-cis-2-hydroxymethyl-4-(cytosin-1'-yl)-1,3-dioxolane (β-OddC-tp) (compound#22).

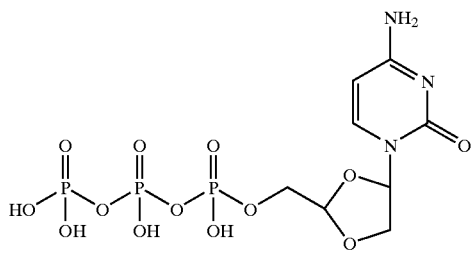

In one embodiment, a compound of formula II is (−)-triphosphate-cis-2-hydroxymethyl-4-(cytosin-1'-yl)-1,3-dioxolane (β-L-OddC-tp) (compound#22 (−)).

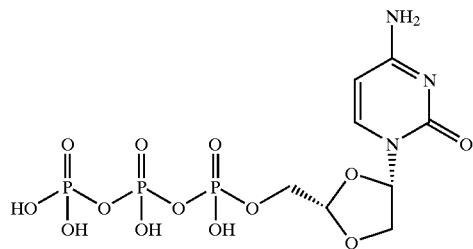

In one embodiment, a compound of formula II is (+)-triphosphate-cis-2-hydroxymethyl-4-(cytosin-1'-yl)-1,3-dioxolane (β-D-OddC-tp) (compound#22 (+)).

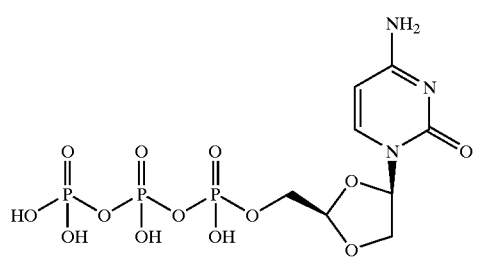

In another embodiment, a compound of formula II is triphosphate-cis-2-hydroxymethyl-4-(5'-fluorocytosin-1'-yl)-1,3-dioxolane(β-5FOddC-tp) (compound#23).

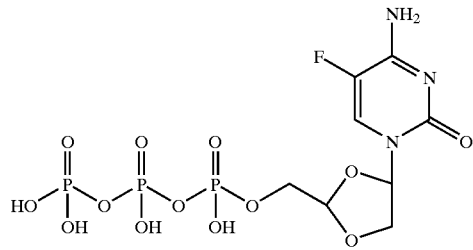

In another embodiment, a compound of formula II is (−)-triphosphate-cis-2-hydroxymethyl-4-(5'-fluorocytosin-1'-yl)-1,3-dioxolane(β-L-5FOddC-tp) (compound#23 (−)).

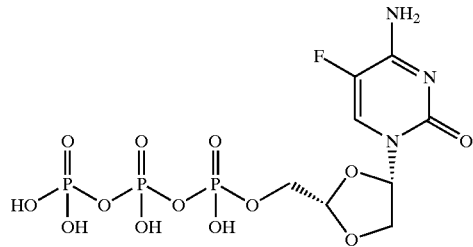

In another embodiment, a compound of formula II is (+)-triphosphate-cis-2-hydroxymethyl-4-(5'-fluorocytosin-1'-yl)-1,3-dioxolane(β-D-5FOddC-tp) (compound#23 (+)).

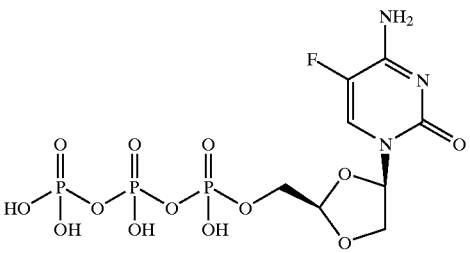

In another embodiment, a compound of formula II is triphosphate-cis-2-hydroxymethyl-4-(5'-azacytosin-1'-yl)-1,3-dioxolane(compound#24).

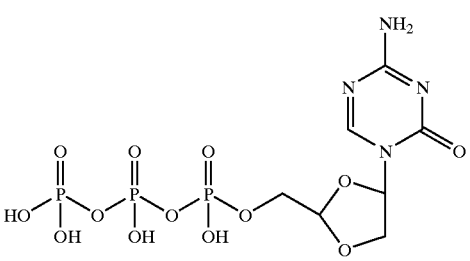

In another embodiment, a compound of formula II is (−)-triphosphate-cis-2-hydroxymethyl-4-(5'-azacytosin-1'-yl)-1,3-dioxolane(compound#24 (−)).

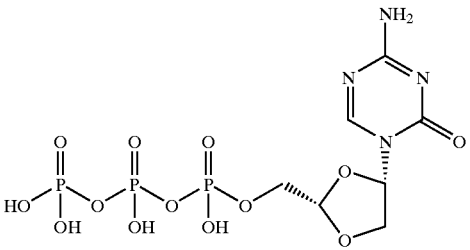

In another embodiment, a compound of formula II is (+)-triphosphate-cis-2-hydroxymethyl-4-(5'-azacytosin-1'-yl)-1,3-dioxolane(compound#24 (+)).

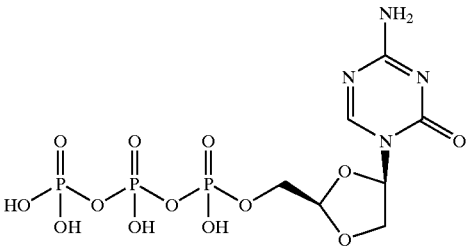

In another embodiment, a compound of formula II is triphosphate-cis-2-hydroxymethyl-4-(5'-methylcytosin-1'-yl)-1,3-dioxolane (compound#25).

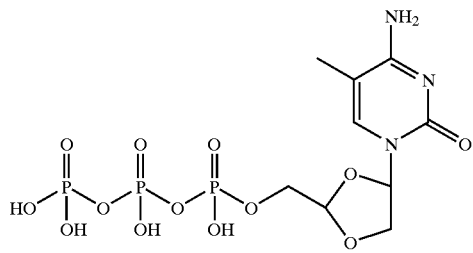

In another embodiment, a compound of formula II is (−)-triphosphate-cis-2-hydroxymethyl-4-(5'-methylcytosin-1'-yl)-1,3-dioxolane (compound#25 (−)).

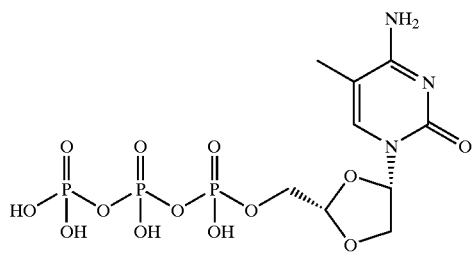

In another embodiment, a compound of formula II is (+)-triphosphate-cis-2-hydroxymethyl-4-(5'-methylcytosin-1'-yl)-1,3-dioxolane(compound#25 (+)).

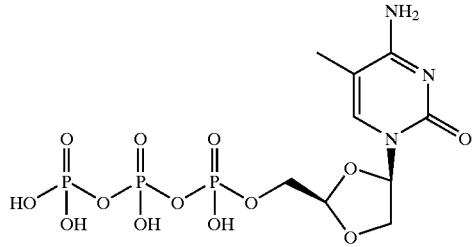

In another embodiment, a compound of formula II is triphosphate-cis-2-hydroxymethyl-4-(N-1'-thyminyl)-1,3-dioxolane (compound#26).

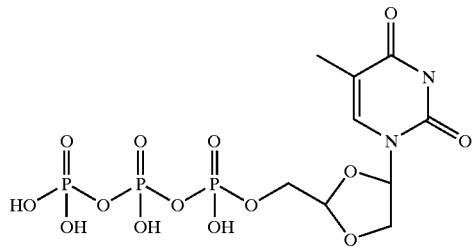

In another embodiment, a compound of formula II is (−)-triphosphate-cis-2-hydroxymethyl-4-(N-1'-thyminyl)-1,3-dioxolane(compound#26 (−)).

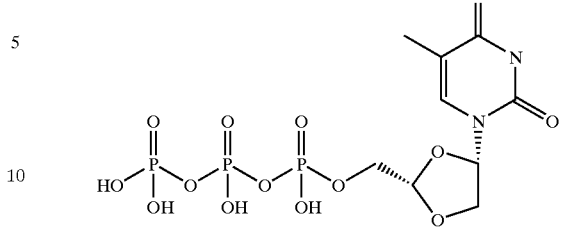

In another embodiment, a compound of formula II is (+)-triphosphate-cis-2-hydroxymethyl-4-(N-1'-thiminyl)-1,3-dioxolane (compound#26 (+)).

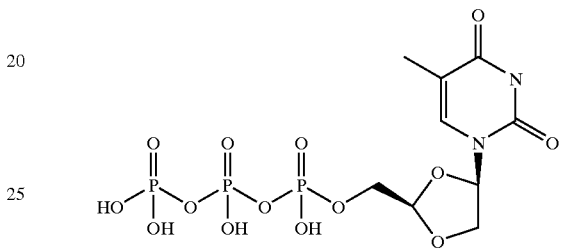

In one embodiment the compounds of the present invention are provided in the form of a single enantiomer at least 95% free of the corresponding enantiomer.

In one embodiment the compounds of the present invention are provided in the form of a single enantiomer at least 95% free of the corresponding enantiomer.

In one embodiment the compounds of the present invention are provided in the form of a single enantiomer at least 99% free of the corresponding enantiomer.

In an other embodiment the compound of the present invention are in the form of the (+) enantiomer at least 95% free of the corresponding (−) enantiomer.

In an other embodiment the compound of the present invention are in the form of the (+) enantiomer at least 97% free of the corresponding (−) enantiomer.

In an other embodiment the compound of the present invention are in the form of the (+) enantiomer at least 99% free of the corresponding (−) enantiomer.

In an other embodiment embodiment, the compound of the present invention are in the form of the (−) enantiomer at least 95% free of the corresponding (+) enantiomer.

In an other embodiment the compound of the present invention are in the form of the (−) enantiomer at least 97% free of the corresponding (+) enantiomer.

In an other embodiment the compound of the present invention are in the form of the (−) enantiomer at least 99% free of the corresponding (+) enantiomer.

There is also provided a pharmaceutically acceptable salts of the present invention. By the term pharmaceutically acceptable salts of compounds of general formula (I) and (II) are meant those derived from pharmaceutically acceptable inorganic and organic acids and bases. Examples of suitable acids include hydrochloric, hydrobromic, sulphuric, nitric, perchloric, fumaric, maleic, phosphoric, glycollic, lactic, salicylic, succinic, toluene-p-sulphonic, tartaric, acetic, citric, methanesulphonic, formic, benzoic, malonic, naphthalene-2-sulphonic and benzenesulphonic acids. Other acids such as oxalic, while not in themselves pharmaceutically acceptable, may be useful as intermediates in obtaining the compounds of the invention and their pharmaceutically acceptable acid addition salts.

Salts derived from appropriate bases include alkali metal (e.g. sodium), alkaline earth metal (e.g. magnesium), ammonium and $NR_{4^+}$ (where R is $C_{1-4}$ alkyl) salts.

References hereinafter to a compound according to the invention includes compounds of the general formula (I) and (II) and there pharmaceutically acceptable salts.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. In case of conflict, the present specification, including definitions, will control. In addition, the materials, methods, and examples are illustrative only and not intended to be limiting.

As used in this application, the term "alkyl" represents an unsubstituted or substituted (by a halogen, nitro, $CONH_2$, COOH, O—$C_{1-6}$ alkyl, O—$C_{2-6}$ alkenyl, O—$C_{2-6}$ alkynyl, hydroxyl, amino, or COOQ, wherein Q is $C_{1-6}$ alkyl; $C_{2-6}$ alkenyl; $C_{2-6}$ alkynyl) straight chain, branched chain or cyclic hydrocarbon moiety (e.g. isopropyl, ethyl, fluorohexyl or cyclopropyl). The term alkyl is also meant to include alkyls in which one or more hydrogen atoms is replaced by an halogen, more preferably, the halogen is fluoro (e.g. $CF_3$— or $CF_3CH_2$—).

The terms "alkenyl" and "alkynyl" represent an alkyl containing at least one unsaturated group (e.g. allyl).

The term "cycloalkyl" represents an alkyl which is cyclic, such as cyclopropyl, cyclopentyl or cyclobutyl.

The term "hydroxy protecting group" is well known in the field of organic chemistry. Such protecting groups may be found in T. Greene, *Protective Groups In Organic Synthesis*, (John Wiley & Sons, 1981). Example of hydroxy protecting groups include but are not limited to acetyl-2-thioethyl ester, pivaloyloxymethyl ester and isopropyloxycarbonyloxymethyl ester.

The term "aryl" represent an unsaturated carbocyclic moiety, optionally mono- or di-substituted with OH, SH, amino, halogen or $C_{1-6}$ alkyl.

The term "heteroaryl" represent an aryl wherein at least one carbon ring atom is substituted by an heteroatom (e.g. N, O, or S).

The term "aminoalkyl" represent an alkyl which is covalently bonded to the adjacent atom through a nitrogen atom.

The term "thioalkyl" represent an alkyl which is covalently bonded to the adjacent atom through a sulfur atom.

The term "alkoxyl" represent an alkyl which is covalently bonded to the adjacent atom through an oxygen atom.

When there is a sulfur atom present, the sulfur atom can be at different oxydation level, S, SO, or $SO_2$. All such oxydation level are within the scope of the present invention.

The term "host" represent any mammals including humans.

In one embodiment, the host is human.

The compounds of the present invention can be prepared by methods well known in the art. For example, such methods are described in the following references: U.S. Pat. No. 5,041,449, PCT publication WO 92/20669 (PCT application PCT/CA92/00211), Journal of Chromatography, 645 (1993) 107–114, Tetrahedron Assymetry Vol. 4 No. 11 pp2319–2322 (1993), Tetrahedron Assymetry Vol. 4 No. 2 pp211–214 (1993), Bioorganic & Medicinal Chemistry Vol.3 No.8, pp.1543–1546 (1993), Tetrahedron Letters, Vol.33, No. 46, pp 6949–6952, (1992), J.Org. Chem., 34(6), 1547–1550 (1969), J.Org. Chem., 52(9), 1794–1801 (1987), J.Am.Chem.Soc., 87(8), 1785–1788 (1965), J.Org. Chem. (1989), 54, 631–635. which are all incorporated by reference.

According to one embodiment, it will be appreciated that the amount of a compound of the present invention required for use in treatment will vary not only with the particular compound selected but also with the route of administration, the nature of the condition for which treatment is required and the age and condition of the patient and will be ultimately at the discretion of the attendant physician or veterinarian. In general however a suitable dose will be in the range of from about 0.01 to about 750 mg/kg of body weight per day, preferably in the range of 0.5 to 60 mg/kg/day, most preferably in the range of 1 to 20 mg/kg/day.

The desired dose according to one embodiment is conveniently presented in a single dose or as divided dose administered at appropriate intervals, for example as two, three, four or more doses per day.

In another embodiment, the compound is conveniently administered in unit dosage form; for example containing 10 to 1500 mg, conveniently 20 to 1000 mg, most conveniently 50 to 700 mg of active ingredient per unit dosage form.

According to another embodiment of the present invention, the active ingredient is administered to achieve peak plasma concentrations of the active compound of from about 1 to about 75 $\mu$M, preferably about 2 to 50 $\mu$M, most preferably about 3 to about 30 $\mu$M. This may be achieved, for example, by the intravenous injection of a 0.1 to 5% solution of the active ingredient, optionally in saline, or orally administered as a bolus containing about 1 to about 500 mg of the active ingredient. Desirable blood levels may be maintained by a continuous infusion to provide about 0.01 to about 5.0 mg/kg/hour or by intermittent infusions containing about 0.4 to about 15 mg/kg of the active ingredient.

While it is possible that, for use in therapy, a compound of the present invention may be administered as the raw chemical, it is preferable according to one embodiment of the invention, to present the active ingredient as a pharmaceutical formulation. The embodiment of the invention thus further provides a pharmaceutical formulation comprising a compound of formula (I),or formula (II), or a pharmaceutically acceptable salt thereof together with one or more pharmaceutically acceptable carriers therefor and, optionally, other therapeutic and/or prophylactic ingredients. The carrier(s) must be "acceptable" in the sense of being compatible with the other ingredients of the formulation and not deleterious to the recipient thereof.

According to one embodiment of the present invention, pharmaceutical formulations include but are not limited to those suitable for oral, rectal, nasal, topical (including buccal and sub-lingual), transdermal, vaginal or parenteral (including intramuscular, sub-cutaneous and intravenous) administration or in a form suitable for administration by inhalation or insufflation. The formulations may, where appropriate, be conveniently presented in discrete dosage units and may be prepared by any of the methods well known in the art of pharmacy. All methods according to this embodiment include the step of bringing into association the active compound with liquid carriers or finely divided solid carriers or both and then, if necessary, shaping the product into the desired formulation.

According to another embodiment, pharmaceutical formulation suitable for oral administration are conveniently presented as discrete units such as capsules, cachets or tablets each containing a predetermined amount of the active ingredient; as a powder or granules. In another embodiment, the formulation is presented as a solution, a suspension or as an emulsion. Still in another embodiment, the active ingredient is presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The compounds of the present invention according to an embodiment are formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing an/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

For topical administration to the epidermis, the compounds, according to one embodiment of the present invention, are formulated as ointments, creams or lotions, or as a transdermal patch. Such transdermal patches may contain penetration enhancers such as linalool, carvacrol, thymol, citral, menthol and t-anethole. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or colouring agents.

Formulations suitable for topical administration in the mouth include lozenges comprising active ingredient in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Pharmaceutical formulations suitable for rectal administration wherein the carrier is a solid. In another embodiment, they are presented as unit dose suppositories. Suitable carriers include cocoa butter and other materials commonly used in the art, and the suppositories may be conveniently formed by admixture of the active compound with the softened or melted carrier(s) followed by chilling and shaping in moulds.

According to one embodiment, the formulations suitable for vaginal administration are presented as pessaries, tampons, creams, gels, pastes, foams or sprays containing in addition to the active ingredient such carriers as are known in the art to be appropriate.

For intra-nasal administration the compounds, in one embodiment of the invention, are used as a liquid spray or dispersible powder or in the form of drops. Drops may be formulated with an aqueous or non-aqueous base also comprising one more dispersing agents, solubilising agents or suspending agents. Liquid sprays are conveniently delivered from pressurized packs.

For administration by inhalation the compounds, according to one embodiment of the invention are conveniently delivered from an insufflator, nebulizer or a pressurized pack or other convenient means of delivering an aerosol spray. In another embodiment, pressurized packs comprise a suitable propellant such as dichlorodifluoromethane, trichlorofluoromethane, dichlorotetrafluoroethane, carbon dioxide or other suitable gas. In another embodiment, the dosage unit in the pressurized aerosol is determined by providing a valve to deliver a metered amount.

Alternatively, in another embodiment, for administration by inhalation or insufflation, the compounds according to the present invention are in the form of a dry powder composition, for example a powder mix of the compound and a suitable powder base such as lactose or starch. In another embodiment, the powder composition is presented in unit dosage form in, for example, capsules or cartridges or e.g. gelatin or blister packs from which the powder may be administered with the aid of an inhalator or insufflator.

In one embodiment, the above described formulations are adapted to give sustained release of the active ingredient.

The compounds of the invention may also be used in combination with other antiviral agents.

In one embodiment, the compounds of the invention may be employed together with at least one other antiviral agent chosen from protease inhibitors, polymerase inhibitors, and helicase inhibitors.

As used in this application, the term "interferon" include: interferon likes molecules such as interferon (IFN), interferon α-2a, interferon α-2b, consensus interferon (CIFN) and other types of interferons.

In one embodiment, the compounds of the invention may be employed together with at least one other antiviral agent chosen from interferon (IFN), interferon α-2a, interferon α-2b, consensus interferon (CIFN), ribavirin, amantadine, rimantadine, interleukine-12, ursodeoxycholic acid (UDCA), glycyrrhizin and silybum marianum.

In one embodiment, the compounds of the invention may be employed together with at least one other antiviral agent chosen from Interferon-α, Ribavirin and Amantadine.

In one embodiment, the compounds of the invention may be employed together with at least one other antiviral agent chosen from Interferon-α and Ribavirin (REBETRON).

In one embodiment, the compounds of the invention may be employed together Interferon-α.

In one embodiment, the compounds of the invention may be employed together with Ribavirin.

The combinations referred to above may conveniently be presented for use in the form of a pharmaceutical formulation and thus pharmaceutical formulations comprising a combination as defined above together with a pharmaceutically acceptable carrier therefor comprise a further aspect of the invention.

The individual components of such combinations may be administered either sequentially or simultaneously in separate or combined pharmaceutical formulations.

When the compound (I), or (II) or a pharmaceutically acceptable salts thereof is used in combination with a second therapeutic agent active against the same virus the dose of each compound may be either the same as or differ from that when the compound is used alone. Appropriate doses will be readily appreciated by those skilled in the art.

The following examples are provided to illustrate various embodiments of the present invention and shall not be considered as limiting in scope.

Scheme 1

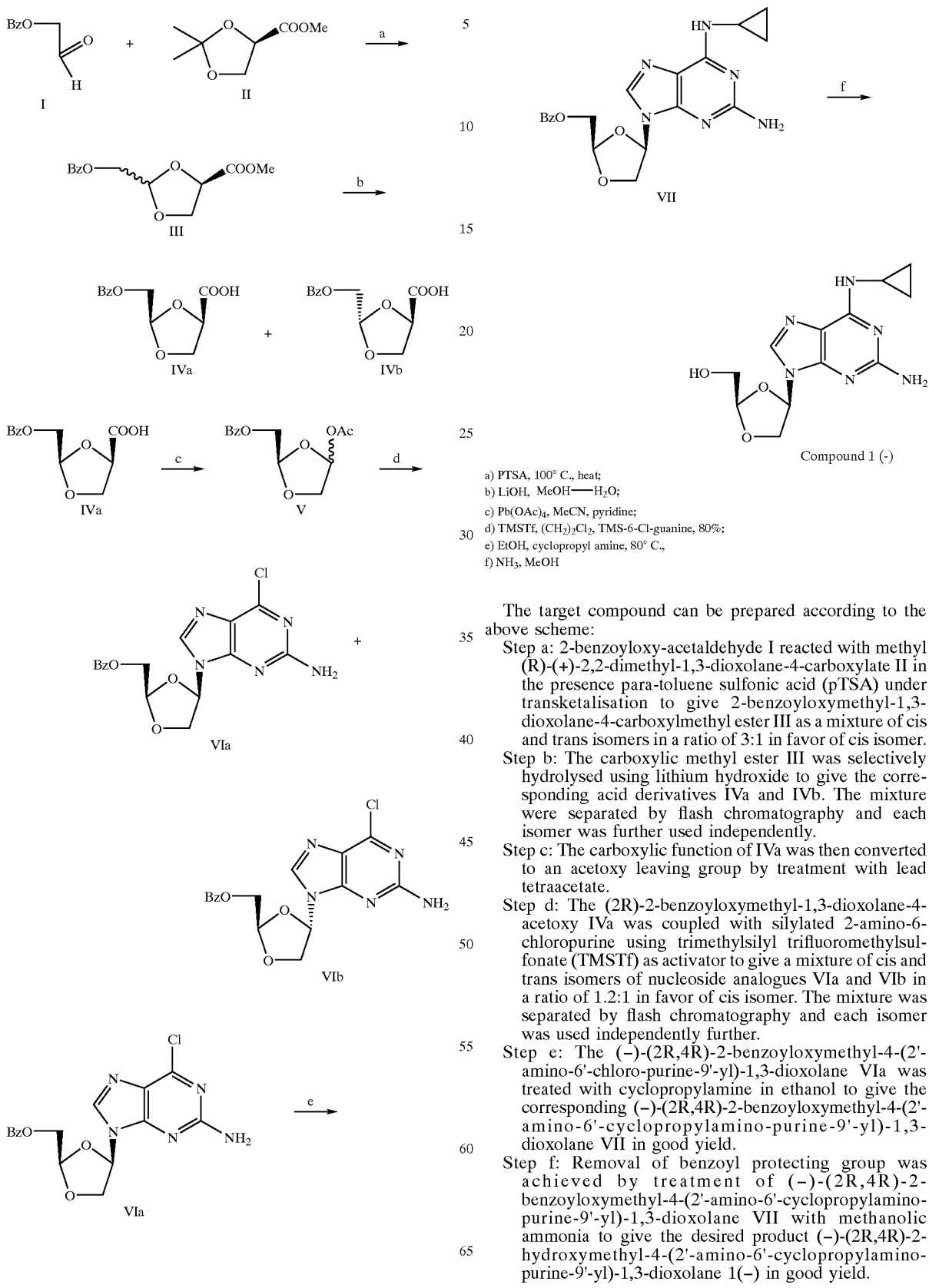

a) PTSA, 100° C., heat;
b) LiOH, MeOH—H$_2$O;
c) Pb(OAc)$_4$, MeCN, pyridine;
d) TMSTf, (CH$_2$)$_2$Cl$_2$, TMS-6-Cl-guanine, 80%;
e) EtOH, cyclopropyl amine, 80° C.,
f) NH$_3$, MeOH The target compound can be prepared according to the above scheme:

Step a: 2-benzoyloxy-acetaldehyde I reacted with methyl (R)-(+)-2,2-dimethyl-1,3-dioxolane-4-carboxylate II in the presence para-toluene sulfonic acid (pTSA) under transketalisation to give 2-benzoyloxymethyl-1,3-dioxolane-4-carboxylmethyl ester III as a mixture of cis and trans isomers in a ratio of 3:1 in favor of cis isomer.

Step b: The carboxylic methyl ester III was selectively hydrolysed using lithium hydroxide to give the corresponding acid derivatives IVa and IVb. The mixture were separated by flash chromatography and each isomer was further used independently.

Step c: The carboxylic function of IVa was then converted to an acetoxy leaving group by treatment with lead tetraacetate.

Step d: The (2R)-2-benzoyloxymethyl-1,3-dioxolane-4-acetoxy IVa was coupled with silylated 2-amino-6-chloropurine using trimethylsilyl trifluoromethylsulfonate (TMSTf) as activator to give a mixture of cis and trans isomers of nucleoside analogues VIa and VIb in a ratio of 1.2:1 in favor of cis isomer. The mixture was separated by flash chromatography and each isomer was used independently further.

Step e: The (−)-(2R,4R)-2-benzoyloxymethyl-4-(2'-amino-6'-chloro-purine-9'-yl)-1,3-dioxolane VIa was treated with cyclopropylamine in ethanol to give the corresponding (−)-(2R,4R)-2-benzoyloxymethyl-4-(2'-amino-6'-cyclopropylamino-purine-9'-yl)-1,3-dioxolane VII in good yield.

Step f: Removal of benzoyl protecting group was achieved by treatment of (−)-(2R,4R)-2-benzoyloxymethyl-4-(2'-amino-6'-cyclopropylamino-purine-9'-yl)-1,3-dioxolane VII with methanolic ammonia to give the desired product (−)-(2R,4R)-2-hydroxymethyl-4-(2'-amino-6'-cyclopropylamino-purine-9'-yl)-1,3-dioxolane 1(−) in good yield.

EXAMPLE 1

Methyl-2-(R,S)-benzoyloxymethyl-1,3-dioxolane-4-(R)-carboxlate.(III)

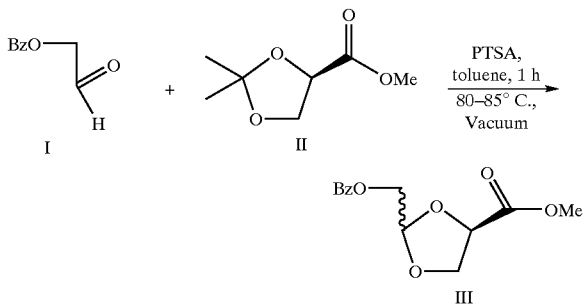

To a solution of methyl-α,β-isopropylidene-D-glycerate (II) (Fluka: registry # 52373-72-5), (9.76 g, 60.9 mmol, 1 eq) and benzoyloxyacetaldehyde I (10 g, 60.9 mmol, 1 eq) in toluene (20 mL) at 80° C., p-toluenesulfonic acid (PTSA) (460 mg, 2.4 mmol, 4 mol %) was added. The reaction flask was kept under vacuum for one hour and a distillate was collected (80–85° C.) during this period of time. The residue was then cooled to room temperature (RT) and purified by column chromatography on silica gel, using hexanes/ethyl acetate as eluent to produce 13.2 g (81%) of the title compound as a mixture of cis and trans isomers in a ratio of 3:1.

Cis isomer:
$^1$H-NMR (CDCl$_3$): δ (ppm): 3.75 (s, 3H, C$\underline{H}_3$); 4.15(dd, 1H, C$_5$—C$\underline{H}$), 4.30 (dd, 1H, C$_5$—C$\underline{H}$); 4.5 (m, 2H, C$\underline{H}_2$—O—CO—C$_6$H$_5$); 4.7 (m, 1H, C$_4$—C$\underline{H}$); 5.4 (t, 1H, C$_2$—C$\underline{H}$); 7.45–8.1 (m, 5H, Ar—C$\underline{H}$).

Trans isomer:
$^1$H-NMR (CDCl$_3$): δ (ppm): 3.8 (s, 3H, C$\underline{H}_3$); 4.1(dd, 1H, C$_5$—C$\underline{H}$); 4.35 (dd, 1H, C$_5$—C$\underline{H}$); 4.45 (m, 2H, C$\underline{H}_2$—O—CO—C$_6$H$_5$); 4.75 (m, 1H, C$_4$—C$\underline{H}$); 5.5 (t, 1H, C$_2$—C$\underline{H}$); 7.45–8.1 (m, 5H, Ar— C$\underline{H}$).

EXAMPLE 2

(2R,4R)-2-benzoyloxymethyl-1,3-dioxolane-4-carboxylic acid.(IVa)

(2S,4R)-2-benzoyloxymethyl-1,3-dioxolane-4-carboxylic acid.(IVb)

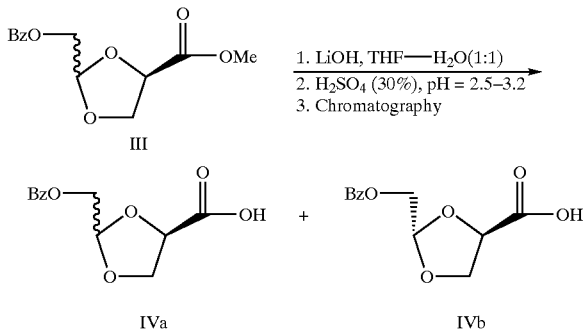

To a solution of methyl-2-(R,S)-benzoyloxymethyl-1,3-dioxolane-4-(R)-carboxylate (III), (411 g, 1.54 mmol, 1 eq., 2:1 mixture of cis and trans isomers) in a 1:1 mixture of tetrahydrofuran (THF) and water, lithium hydroxide (LiOH) (64.8 g, 1.54 moles, 1 eq) was added portion wise over a period of 30 min., keeping the reaction flask temperature below 30° C. After 90 min., THF was removed by vacuum and the aqueous solution was acidified to pH=2.5–3.2, by dropwise addition of 30% (w/w) sulphuric acid. The resulting solution was extracted with dichloromethane (4×400 mL). The combined organic phase was washed with brine, dried over sodium sulphate and concentrated to produce 380 g of a dark oil. The isomers were separated by column chromatography on silica gel, using 2% acetic acid in dichloromethane to produce 220 g of the cis isomer (IVa) (56.5%) and 116 g of the trans isomer (IVb) (30%). Each of isomers was independently used for next step.

Cis isomer:
(2R,4R)-2-benzoyloxymethyl-1,3-dioxolane-4-carboxylic acid.(IVa)
$^1$H-NMR (CDCl$_3$): δ (ppm): 4.2 (t, 1H, C$_5$—$\underline{H}$); 4.4 (m, 1H); 4.5 (m, 1H); 4.7 (m, 2H); 5.4 (t, 1H, C$_2$—C$\underline{H}$); 7.45–8.1 (m, 5H, Ar—C$\underline{H}$); 7.2–8.0(bs, 1H, COO$\underline{H}$).

Trans isomer:
(2S,4R)-2-benzoyloxymethyl-1,3-dioxolane-4-carboxylic acid.(IVb)
$^1$H-NMR (CDCl$_3$): δ (ppm): 4.15 (dd, 1H, C$_5$—$\underline{H}$); 4.4 (t, 1H, C$_5$—$\underline{H}$); 4.45 (m, 2H, C$\underline{H}_2$—OCOC$_6$H$_5$); 4.8 (dd, 1H, C$_4$—C$\underline{H}$); 5.6 (t, 1H, C$_2$—C$\underline{H}$); 7.45–8.1 (m, 5H, Ar—C$\underline{H}$); 8.3–8.8 (bs, 1H, COO$\underline{H}$).

EXAMPLE 3

(2R)-2-benzoyloxymethyl-4-(R,S)-acetoxy-1,3-dioxolane.(V)

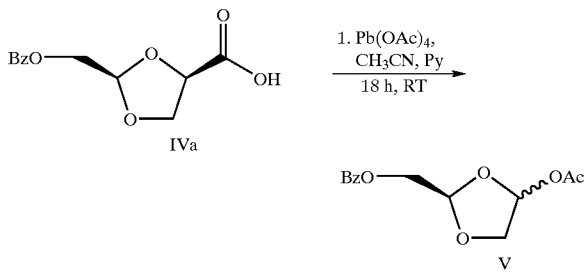

To a solution of (2R,4R)-2-benzoyloxymethyl-1,3-dioxolane-4-carboxylic acid (IVa), (130 g, 0.515 moles, 1 eq) and pyridine (60 mL, 0.741 moles, 1.44 eq) in acetonitrile at 4° C., lead tetraacetate, (assay 95%, 300 g, 0.678 moles, 1.25 eq) was added over a period of 20 min. The reaction mixture was kept under stirring for 18 hours at room temperature (RT). The inorganics were removed by filtration, the filtrate was poured on to a saturated solution of sodium bicarbonate (2 L) followed by addition of solid sodium bicarbonate (pH=7–8). The organic phase was separated, and the aqueous phase was extracted with ethyl acetate (3×400 mL). The combined organic phase was concentrated and purified by column chromatography, on silica gel, using hexanes/ethyl acetate as eluent to produce 93.5 g (68%) of the title compound as a mixture of cis and trans isomers in a ratio of 2:1 (V). The mixture was used for next step.

cis/trans isomers:
$^1$H-NMR (CDCl$_3$): δ (ppm): 2.0,2.15 (s, 3H, C$\underline{H}_3$); 4.05–4.45 (m, 4H, C$\underline{H}$); 5.45, 5.55 (t, 1H, C$_2$—C$\underline{H}$); 6.4, 6.45 (dd, 1H, C$_4$—C$\underline{H}$); 7.45–8.1 (m, 5H, Ar—C$\underline{H}$);

EXAMPLE 4

(2R,4R) and (2R,4S)-2-benzoyloxymethyl-4-(2'-amino-6'-chloro-purine-9'-yl)-1,3-dioxolane (VIa and VIb)

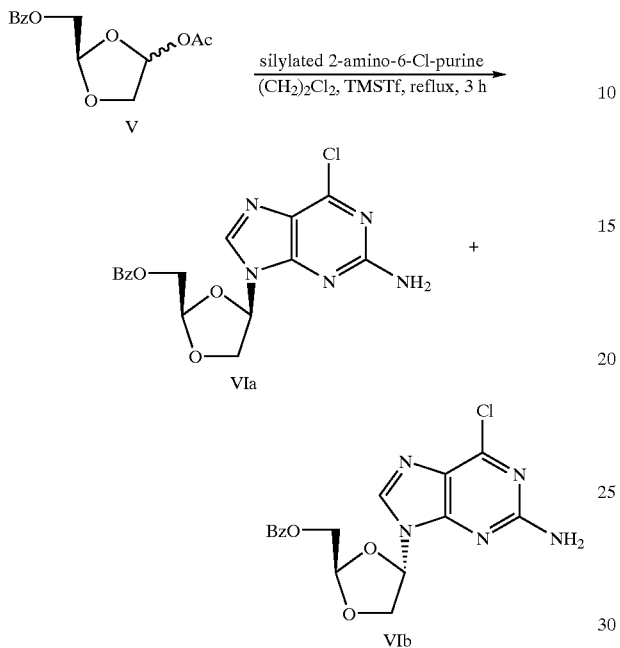

2-amino-6-chloro-purine (4.15 g, 1.3 eq.) in 50 ml of hexamethyldisilazane(HMDS) containing 100 mg of ammonium sulfate was heated under reflux for 3 h after which time the clear solution was evaporated to dryness in vacuo. The residue was dissolved in 100 mL of anhydrous 1,2-dichloroethane. (2R)-2-benzoyloxymethyl-4-acetoxy-1,3-dioxolane (V)(5 g) was dried by co-evaporation twice with benzene (2×30 mL) and dissolved in 100 mL of anhydrous 1,2-dichloroethane. The solution was then transferred into the reaction flask containing silylated 2-amino-6-chloro-purine solution. The mixture was placed in a 60° C. preheated oil bath for 15 minutes, followed the addition of trimethylsilyl triflate (TMS-OTf) (3.8 mL, 1.1 eq.). The mixture was heated at refluxing under nitrogen for 3 h and the solution became brown. TLC (hex:EtOAc 7:3 for sugar and hex:EtOAc 1:4 for product) indicated a completed reaction with the disappearance of sugar and the presence of two well separated spots for cis and trans products. The reaction mixture was cooled to room temperature, poured into a saturated sodium bicarbonate solution (100 mL) and stirred for 10 minutes. The organic layer was collected and the aqueous layer was extracted twice with methylene chloride (2×50 ml). The combined organic solution was washed with water, brine and dried over $MgSO_4$ as usual. and solvent was evaporated to dryness to give a foam (7 g). H-NMR of the crude indicated clean reaction with cis and trans products in a ratio of 1.2:1 in favor of cis isomer. The crude product was purified on silica gel using a gradient of hexane:ethyl acetate 7:3, 1:1 and 2:3 as eluant to yield 2.5 g of trans isomer (less polar, α-anomer)(VIb) as a foam, which was crystallized in EtOH and 3 g of cis isomer (more polar, β-anomer) (VIa) as a foam, which was crystallized in EtOH and 0.3 g of mixture cis and trans in favor of cis as a foam for a total of 82% yield.

Trans isomer:

(+)-(2R,4S)-2-benzoyloxymethyl-4-(2'-amino-6'-chloro-purine-9'-yl)-1,3-dioxolane (VIb)

$R_f$:0.40 (hexane-EtOAc 3:7)

$[\alpha_D]$ +21.16° (c 0.293 in $CH_2Cl_2$)

$^1$H-NMR (CDCl$_3$): δ (ppm): 4.45–4.55 (m, 4H; C$_5$—H$_2$, C$_2$—CH$_2$—OBz), 5.16 (b, 2H, NH$_2$), 5.83 (t, 1H, C$_2$—H, J=3.8 Hz), 6.39 (dd, 1H, C$_4$—H), 7.45 (t, 2H, aromatic), 7.62 (t, 1H, aromatic), 7.92 (s, 1H, C$_{8'}$—H), 8.10 (d, 2H, aromatic).

U.V.: (CH$_3$OH) $\lambda_{max}$: 312 nM

Cis isomer:

(−)-(2R,4R)-2-benzoyloxymethyl-4-(2'-amino-6'-chloro-purine-9'-yl)-1,3-dioxolane (VIa)

$R_f$:0.26 (hexane-EtOAc 3:7)

$[\alpha_D]$ −87.7° (c 0.2565 in $CH_2Cl_2$)

$^1$H-NMR (CDCl$_3$): δ (ppm): 4.25–4.33 (dd, 1H, C$_5$—H), 4.60–4.64 (m, 3H ; C$_5$—H and C$_2$—CH$_2$—OBz), 5.17 (b, 2H, NH$_2$), 5.42 (t, 1H, C$_2$—H, J=3.5 Hz), 6.33 (dd, 1H, C$_4$—H), 7.45 (t, 2H, aromatic), 7.62 (t, 1H, aromatic), 7.95 (d, 2H, aromatic), 8.05 (s, 1H, C$_{8'}$—H).

U.V.: (CH$_3$OH) $\lambda_{max}$: 312 nM.

EXAMPLE 5

(−)-(2R,4R)-2-benzoyloxymethyl-4-(2'-amino-6'-cyclopropylamino-purine-9'-yl)-1,3-dioxolane (VII)

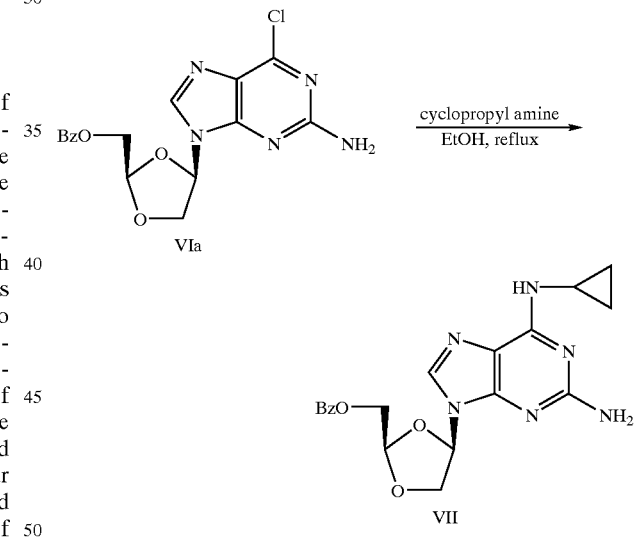

To a solution of (−)-(2R,4R)-2-benzoyloxymethyl-4-(2'-amino-6'-chloro-purine-9'-yl)-1,3-dioxolane (VIa)(600 mg) in ethanol (30 mL) was added cyclopropylamine (2 mL, =18 eq.). The mixture was gently heated at reflux (80–85° C.) for 18 h and cooled to room temperature. Solvent was evaporated to dryness in vacuo. The residue was dissolved in 100 mL of methylene chloride, washed with saturated NaHCO$_3$ solution, water, brine and dried over MgSO$_4$. Solvent was removed in vacuo and residue was purified on silica gel using EtOAc:MeOH as eluant to give the desired product (VII) as a foam in 80% yield.(506 mg).

$R_f$:0.26 (CH$_2$Cl$_2$:MeOH 95:5)

$[\alpha_D]$ −67.7° (c 0.2565 in CH$_2$Cl$_2$)

$^1$H-NMR (CDCl$_3$): δ (ppm): 0.64–0.68 (m, 2H, CH$_2$ of cyclopropyl), 0.91–0.96 (m, 2H, CH$_2$ of cyclopropyl), 3.06

(b, 1H, CH of cyclopropyl), 4.27–4.30 (dd, 1H, C$_5$—H), 4.54–4.57 (dd, 1H ; C$_5$—H) 4.60 (t, 2H, C$_2$—C$\underline{H}_2$—OBz), 5.37 (b, 2H, NH$_2$), 5.42 (t, 1H, C$_2$—H, J=3.5 Hz), 6.28 (b, 1H, NH), 6.35 (dd, 1H, C$_4$—H), 7.45 (t, 2H, aromatic), 7.58 (t, 1H, aromatic), 7.77 (s, 1H, C$_{8'}$-8), 8.01(d, 2H, aromatic), U.V.: (CH$_3$OH) $\lambda_{max}$: 283 and 260 nM.

EXAMPLE 6

(−)-(2R,4R)-2-hydroxymethyl-4-(2'-amino-6'-cyclopropylamino-purine-9'-yl)-1,3-dioxolane (compound 1(−))

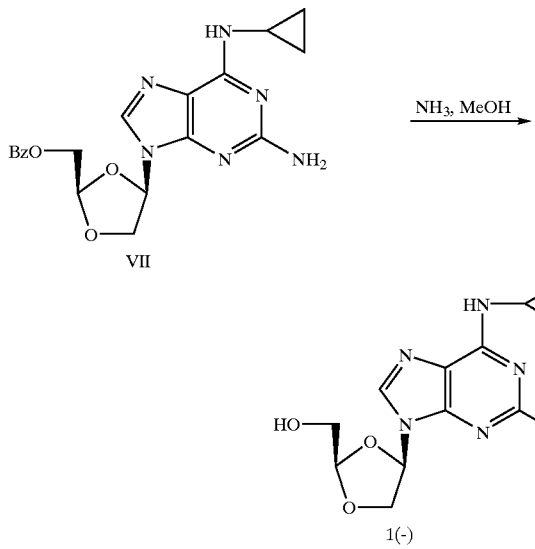

A solution of (−)-(2R,4R)-2-benzoyloxymethyl-4-(2'-amino-6'-cyclopropylamino-purine-9'-yl)-1,3-dioxolane (VII) (480 mg) in 30 mL of saturated methanolic ammonia was stirred at room temperature for 18 h. The mixture was evaporated to dryness in vacuo. The residue was dissolved in 20 mL of water, washed twice with 10 mL of methylene chloride and lyophilized to give 283 mg of white solid in 80% yield (1(−)).

R$_f$:0.26 (CH$_2$Cl$_2$:MeOH 9:1)

[α$_D$] −35.9° (c 0.334 in MeOH)

$^1$H-NMR (DMSO$_{d-6}$): δ (ppm): 0.55 (m, 2H, CH$_2$ of cyclopropyl), 0.95 (m, 2H, CH$_2$ of cyclopropyl), 3.15 (b, 1H, CH of cyclopropyl), 3.80 (m, 2H, C$\underline{H}_2$OH), 4.30 (dd, 1H, C$_5$—H), 4.55 (dd, 1H ; C$_5$—H), 5.08 (t, 1H, C$_2$—H), 5.17 (b, H, OH), 6.15 (b, 2H, NH$_2$), 6.52 (dd, 1H, C$_4$—H), 7.72 (b, 1H, NH), 8.12 (s, 1H, C$_{8'}$-8).

U.V.: (CH$_3$OH) $\lambda_{max}$: 283 and 260 nM.

EXAMPLE 7

(−)-(2R,4R)-2-benzoyloxymethyl-4-(2'-amino-6'-cyclobutylamino-purine-9'-yl)-1,3-dioxolane

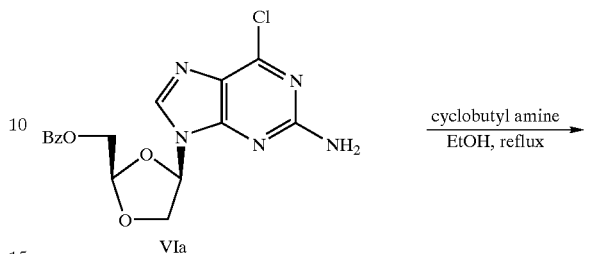

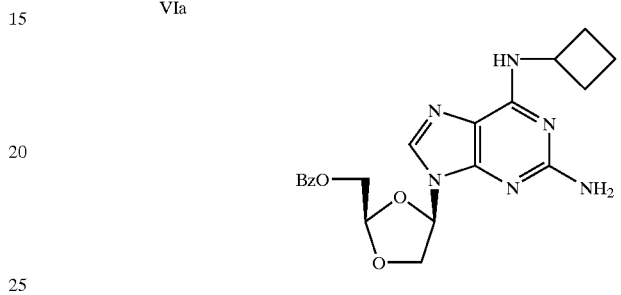

To a solution of (−)-(2R,4R)-2-benzoyloxymethyl-4-(2'-amino-6'-chloro-purine-9'-yl)-1,3-dioxolane (VIa)(250 mg) in ethanol (25 ml) was added cyclobutylamine (0.17 mL, =3 eq.). The mixture was gently heated at reflux (80–85° C.) for 18 h and cooled to room temperature. Solvent was evaporated to dryness in vacuo. The residue was dissolved in 100 mL of methylene chloride, washed with saturated NaHCO$_3$ solution, water, brine and dried over MgSO$_4$. Solvent was removed in vacuo and residue was purified on silica gel using EtOAc:MeOH 95:5 as eluant to give the desired product as a foam in 84% yield.(230 mg).

R$_f$:0.31 (CH$_2$Cl$_2$:MeOH 95:5)

[α$_D$] −62.5° (c 0.4925 in CH$_2$Cl$_2$)

$^1$H-NMR (CDCl$_3$): δ (ppm):1.74–1.78 (m, 2H, CH$_2$ of cyclobuyl), 1.95–2.00 (m, 2H, CH$_2$ of cyclobutyl), 2.43–2.45 (m, 2H, CH$_2$ of cyclobutyl), 4.27–4.30 (dd, 1H, C$_5$—H), 4.54–4.57 (dd, 1H ; C$_5$—H), 4.59 (t, 2H, C$_2$—C$\underline{H}_2$—OBz), 4.75 (b, 1H, CH of cyclobutyl), 5.37 (b, 2H, NH$_2$), 5.41 (t, 1H, C$_2$—H, J=3.6 Hz), 6.00 (b, 1H, NH), 6.35 (dd, 1H, C$_4$—H), 7.45 (t, 2H, aromatic), 7.58 (t, 1H, aromatic), 7.75 (s, 1H, C$_{8'}$—H), 8.01 (d, 2H, aromatic), U.V.: (CH$_3$OH) $\lambda_{max}$: 283 and 263 nM.

EXAMPLE 8

(−)-(2R,4R)-2-hydroxymethyl-4-(2'-amino-6'-cyclobutylamino-purine-9'-yl)-1,3-dioxolane (compound 2(−))

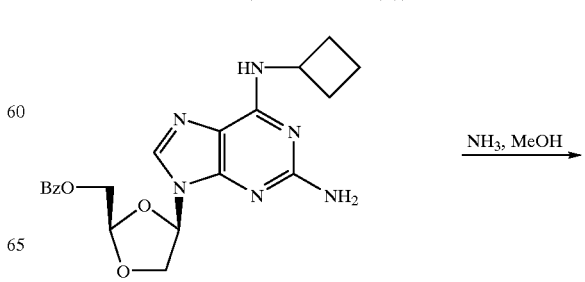

33

-continued

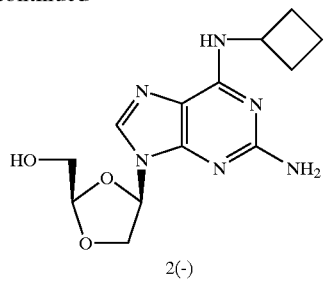

2(−)

A solution of (−)-(2R,4R)-2-benzoyloxymethyl-4-(2'-amino-6'-cyclobutylamino-purine-9'-yl)-1,3-dioxolane (214 mg) in 20 mL of saturated methanolic ammonia was stirred at room temperature for 18 h. The mixture was evaporated to dryness in vacuo. The residue was dissolved in 20 mL of water, washed twice with 10 mL of ether and evaporated to dryness by coevaporation with ethanol to give 154 mg of pure product (2(−)). as a foam in 96% yield.

$R_f$:0.52 (CH$_2$Cl$_2$:MeOH 9:1)

[$\alpha_D$] −29.04° (c 0.396 in MeOH)

$^1$H-NMR (DMSO$_{d-6}$): δ (ppm): 1.61 (m, 2H, CH$_2$ of cyclobutyl), 2.06 (m, 2H, CH$_2$ of cyclobutyl), 2.18 (m, 2H, CH$_2$ of cyclobutyl), 3.58 (m, 2H, C$\underline{H}_2$OH), 4.17 (dd, 1H, C$_5$—H), 4.40 (dd, 1H ; C$_5$—H), 4.90 (b, 1H, CH of cyclobutyl), 5.01 (t, 1H, C$_2$—H), 5.42 (b, H, OH), 5.87 (b, 2H, NH$_2$), 6.19 (dd, 1H, C$_4$—H) 7.62 (b, 1H, NH), 7.85 (s, 1H, C$_{8'}$-8).

U.V.: (CH$_3$OH) $\lambda_{max}$: 283 and 260 nM.

EXAMPLE 9

(−)-(2R,4R)-2-benzoyloxymethyl-4-(2'-amino-6'-cyclopentylamino-purine-9'-yl)-1,3-dioxolane

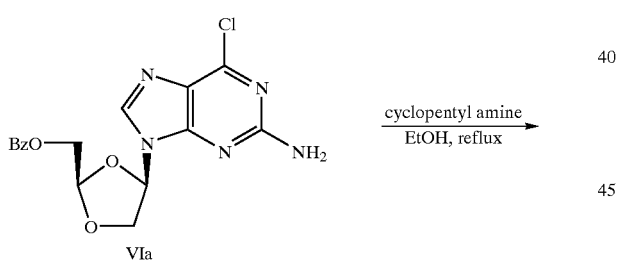

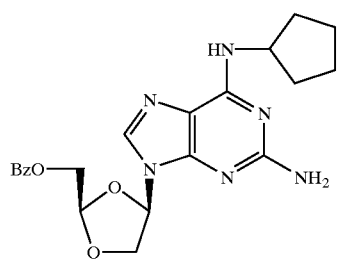

To a solution of (−)-(2R,4R)-2-benzoyloxymethyl-4-(2'-amino-6'-chloro-purine-9'-yl)-1,3-dioxolane (VIa)(250 mg) in ethanol (15 mL) was added cyclopentylamine (0.2 mL, ≈3 eq.). The mixture was gently heated at reflux (80–85° C.) for 18 h and cooled to room temperature. Solvent was evaporated to dryness in vacuo. The residue was dissolved in 100 mL of methylene chloride, washed with saturated NaHCO$_3$ solution, water, brine and dried over MgSO$_4$. Solvent was

34 removed in vacuo and residue was purified on silica gel using EtOAC and EtOAc:MeOH 95:5 as eluant to give the desired product as a foam in 70% yield.(191 mg).

$R_f$:0.30 (CH$_2$Cl$_2$:MeOH 95:5)

[$\alpha_D$] −67.7° (c 0.363 in CH$_2$Cl$_2$)

$^1$H-NMR (CDCl$_3$): δ (ppm): 1.53 (m, 2H, CH$_2$ of cyclopentyl), 1.68 (m, 2H, CH$_2$ of cyclopentyl), 1.76 (m, 2H, CH$_2$ of cyclopentyl), 2.10 (m, 2H, CH$_2$ of cyclopentyl), 4.25 (dd, 1H, C$_5$—H), 4.54–4.54–4.60 (m, 4H ; C$_5$—H, C$_2$—C$\underline{H}_2$—OBz and CH of cyclopentyl), 4.98 (b, 2H, NH$_2$), 5.42 (t, 1H, C$_2$—H, J=3.5 Hz), 5.75 (b, 1H, NH), 6.35 (d, 1H, C$_4$—H), 7.45 (t, 2H, aromatic), 7.58 (t, 1H, aromatic), 7.74 (s, 1H, C$_{8'}$—H), 8.01 (d, 2H, aromatic), U.V.: (CH$_3$OH) $\lambda_{max}$: 283 and 260 nM.

EXAMPLE 10

(−)-(2R,4R)-2-hydroxymethyl-4-(2'-amino-6'-cyclopentylamino-purine-9'-yl)-1,3-dioxolane (compound 3(−))

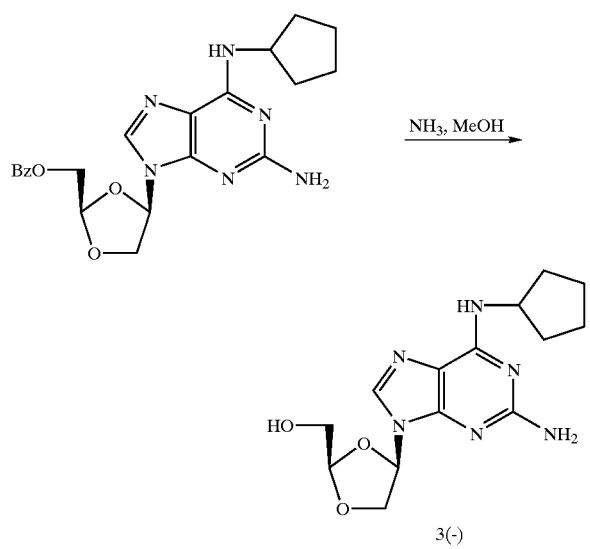

3(−)

A solution of (−)-(2R,4R)-2-benzoyloxymethyl-4-(2'-amino-6'-cyclopentylamino-purine-9'-yl)-1,3-dioxolane (180 mg) in 20 mL of saturated methanolic ammonia was stirred at room temperature for 18 h. The mixture was evaporated to dryness in vacuo. The residue was purified on silica gel using CH$_2$Cl$_2$:MeOH 95:5 as eluant to give 130 mg of white solid (3(−)) in 95% yield.

$R_f$:0.58 (CH$_2$Cl$_2$:MeOH 9:1)

[$\alpha_D$] −30.2° (c 0.4275 in MeOH)

$^1$H-NMR (DMSO$_{d-6}$): δ (ppm): 1.55 (m, 4H, CH$_2$ of cyclopentyl), 1.68 (m, 2H, CH$_2$ of cyclopentyl), 1.88 (m, 2H, CH$_2$ of cyclopentyl), 3.58 (m, 2H, C$\underline{H}_2$OH), 4.17 (dd, 1H, C$_5$—H), 4.41 (dd, 1H ; C$_5$—H), 4.5 (b, 1H, CH of cyclopentyl), 5.01 (t, 1H, C$_2$—H), 5.14 (b, H, OH), 5.85 (b, 2H, NH$_2$), 6.18 (dd, 1H, C$_4$—H), 7.12 (b, 1H, NH), 7.84 (s, 1H, C$_{8'}$—H).

U.V.: (CH$_3$OH) $\lambda_{max}$: 283 and 260 nm.

EXAMPLE 11

Preparation of (+)-cis-2-hydroxymethyl-4-(cytosin-1'-yl)-1,3-dioxolane (β-D-OddC) (compound#17(+)) and (+)-triphosphate-cis-2-hydroxymethyl-4-(cytosin-1'-yl)-1,3-dioxolane (β-D-OddC-tp) (compounds #22(+))

Scheme 2

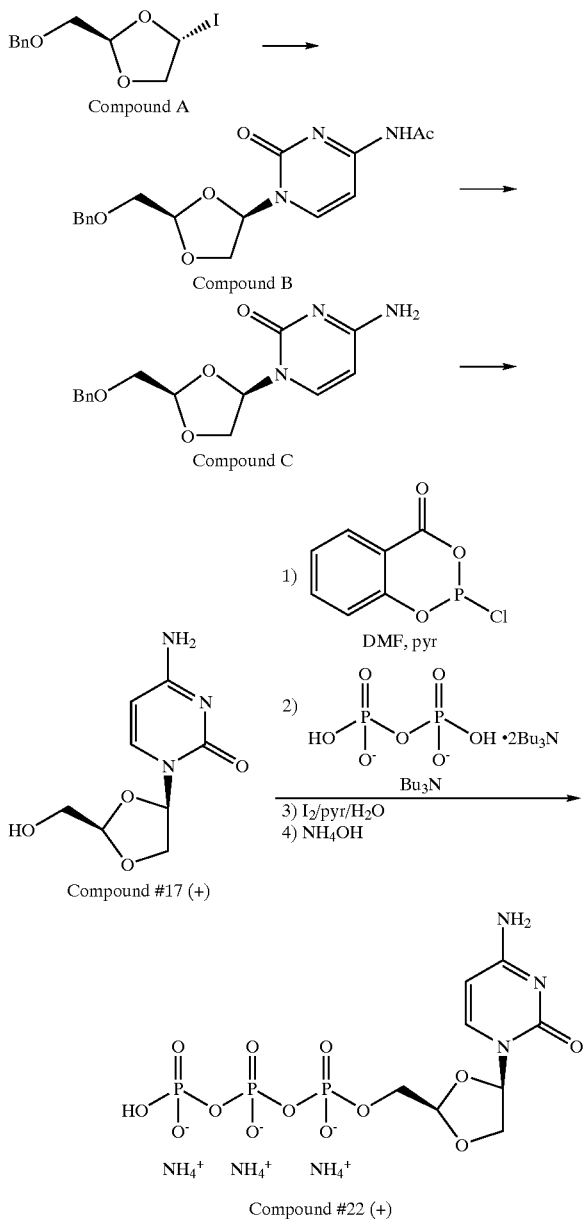

To a stirring suspension of 4-amino-1-(2-(R)-hydroxymethyl-[1,3]dioxolan-4-(R)-yl)-1H-pyrimidin-2-one (17(+)) (18.8 mg, 0.088 mmol) in dry DMF (0.49 mL) was added dry pyridine (0.13 mL) followed by a freshly prepared solution of 2-chloro-4H-1,3,2-benzodioxaphosphorin-4-one 1.0 M in 1,4-dioxane (81 μL, 0.081 mmol). The mixture was stirred 15 minutes at room temperature, then tributylamine (53 μL, 0.22 mmol) and a solution of tributylammonium pyrophosphate 0.42 M in DMF (175 μL, 0.073 mmol) were added simultaneously. The mixture was stirred another 15 minutes. A solution of I2 1% in pyridine/H2O (98:2) (1.4 mL, 0.115 mmol of I) was added and the mixture was stirred 15 minutes. The excess of iodine was destroyed by adding 0.5 mL of aqueous sodium bisulfite 5%. The mixture was stirred 15 minutes, then it was concentrated under reduced pressure to remove all solvents. The residue was dissolved in water, washed two times with methylene chloride and once with ethyl acetate. The aqueous layer was concentrated and purified by charcoal column as follow: about 400 mg of charcoal, placed over a thin layer of Celite in a funnel with fritted disk, was prewashed by passing methanol, then water (by vaccuum). The crude residue was diluted in a minimum of water, acidified to pH 1–2 by adding few drops of HCl 1N, then placed on the top of the charcoal column. The column was eluted with water (25 mL) in order to remove inorganic salts, then 0.5 N ammonia (10 mL) to collect the desired triphosphate. The collected triphophate was lyophilized, and it was then purified again on a small pad of charcoal, this time eluting only with water. The desired triphosphate comes out fast. Few fractions were collected and lyophilized to give the triphosphate ammonium salt (22(+)), as a yellow solid (4.8 mg, 13% yield).

$^1$H NMR (400 MHz, D$_2$O) δ ppm: 7.93 (d, 1 H, 7.47 Hz), 6.21 (s, 1 H), 6.02 (d, 1 H, 7.47 Hz), 5.19 (s, 1 H), 4.20 (m, 4 H).

$^{31}$P NMR (162 MHz, D$_2$O) δ ppm: −6.1 (d, 19 Hz), −10.5 (d, 19 Hz), −21.7 (t, 19 Hz).

The compounds of the present invention can be prepared by methods well known in the art. For example, such methods are described in the following references: U.S. Pat. No. 5,041,449, PCT publication Wo 92/20669 (PCT application PCT/CA92/00211), Journal of Chromatography, 645 (1993) 107–114, Tetrahedron Assymetry Vol. 4 No. 11 pp.2319–2322 (1993), Tetrahedron Assymetry Vol. 4 No. 2 pp.211–214 (1993), Bioorganic & Medicinal Chemistry Vol.3 No.8, pp.1543–1546 (1993), Tetrahedron Letters, Vol.33, No. 46, pp 6949–6952, (1992), J.Org. Chem., 34(6), pp.1547–1550 (1969), J.Org. Chem., 52(9), pp.1794–1801 (1987), J.Am.Chem.Soc., 87(8), pp.1785–1788 (1965), J.Org. Chem. (1989), 54, pp.631–635 which are all incorporated by reference.

In a similar manner, the following compounds were synthesized:

(−)Cis-2-hydroxymethyl-4-(5'-cytosin-1'-yl)-1,3-Dioxolane (Compound #17(−))
(+)Cis-2-hydroxymethyl-4-(5'-cytosin-1'-yl)-1,3-Dioxolane (Compound #17 (+))
(+)Cis-2-hydroxymethyl-4-(5'-fluorocytosin-1'-yl)-1,3-Dioxolane (Compound#18(+))
(−)Cis-2-hydroxymethyl-4-(5'-fluorocytosin-1'-yl)-1,3-Dioxolane (Compound#18 (−))
(+)Cis-2-hydroxymethyl-4-(5'-azacytosin-1'-yl)-1,3-Dioxolane (Compound#19 (+))
(−)Cis-2-hydroxymethyl-4-(5'-azacytosin-1'-yl)-1,3-Dioxolane (Compound#19 (−))
(−)-cis-2-hydroxymethyl-4-(5'-methylcytosin-1'-yl)-1,3-dioxolane(β-L-) (compound#20 (−)).
(+)-cis-2-hydroxymethyl-4-(5'-methylcytosin-1'-yl)-1,3-dioxolane (compound#20 (+)).
(−)-cis-2-hydroxymethyl-4-(N-1'-thyminyl)-1,3-dioxolane (compound#21 (−)).
(+)-cis-2-hydroxymethyl-4-(N-1'-thyminyl)-1,3-dioxolane (compound#21 (+))

EXAMPLE 12

Evaluation of Nucleoside Triphosphate Analogues in the HCV RNA-Dependent RNA Polymerase Assay The following references which are referenced in the example are all incorporated by reference:

1. Behrens, S., Tomei, L., De Francesco, R. (1996) *EMBO* 15, pp.12–22
2. Harlow, E, and Lane, D. (1988) *Antibodies: A Laboratory Manual.* Cold Spring Harbord Laboratory. Cold Spring Harbord, N.Y.
3. Lohmann, V., Körner, F., Herian, U., and Bartenschlager, R. (1997) *J. Virol.* 71, pp.8416–8428

Compounds were evaluated using an in vitro polymerase assay containing purified recombinant HCV RNA-dependent RNA polymerase (NS5B protein). HCV NS5B was expressed in insect cells using a recombinant baculovirus as vector. The experimental procedures used for the cloning, expression and purification of the HCV NS5B protein are described bellow. Follows, are details of the RNA-dependent RNA polymerase assays used to test the compounds.

Expression of the HCV NS5B Protein in Insect Cells

The cDNA encoding the entire NS5B protein of HCV-Bk strain, genotype 1b, was amplified by PCR using a plasmid containing a cDNA version of the full-length HCV genome as template. The oligonucleotides used to amplify this HCV region were designed to introduce a NheI site followed by an ATG at the 5' end of the NS5B coding region as well as a BamHI site at the 3'end immediately downstream of the translation stop codon. The amplified sequence, of 1.8 kb, was digested with NheI and BamHI and ligated to a predigested pBlueBacII plasmid (Invitrogen). The resulting recombinant plasmid was designated pBac/NS5B. Sf9 cells were co-transfected with 3 µg of pBac/NS5B, together with 1 µg of linearized baculovirus DNA (Invitrogen), as described in the manufacturer's protocol. Following two rounds of plaque purification, an NS5B-recombinant baculovirus, BacNS5B, was isolated. The presence of the recombinant NS5B protein was determined by western blot analysis (Harlow and Lane, 1988) of BacNS5B-infected Sf9 cells, using a HCV NS5B specific rabbit polyclonal antiserum (anti-NS5B). Infections of Sf9 cells with this plaque purified virus were performed in one-liter spinner flasks at a cell density of $1.2 \times 10^6$ cells/ml and a multiplicity of infection of 5.

Preparation of a Soluble Recombinant NS5B Protein

Sf9 cells were infected as described above. Sixty hours post-infection, cells were harvested then washed twice with phosphate buffer saline (PBS). Total proteins were solubilized as described in Lohmann et al. (1997) with some modifications. In brief, proteins were extracted in three steps, S1, S2, S3, using lysis buffers (LB) I, LB II and LB III (Lohmann et al, 1997). The composition of LBII was modified to contain 0.1% triton X-100 and 150 mM NaCl to reduce the amount of solubilized NS5B protein at this step. In addition, sonication of cell extracts was avoided throughout the protocol to preserve the integrity of the protein structure.

Purification of Recombinant NS5B Using Fast Protein Liquid Chromatography (FPLC)

Soluble NS5B protein in the S3 fraction was diluted to lower the NaCl concentration to 300 mM, then it incubated batchwise with DEAE sepharose beads (Amersham-Pharmacia) for 2 hrs at 4° C., as described by Behrens et al. (1996). Unbound material was cleared by centrifugation for 15 min at 4° C., at 25000 rpm using a SW41 rotor (Beckman). The supernatant was further diluted to lower the NaCl concentration to 200 mM and subsequently loaded, with a flow rate of 1 ml/min, on a 5 ml HiTrap® heparin column (Amersham-Pharmacia) connected to an FPLC® system (Amersham-Pharmacia). Bound proteins were eluted in 1 ml fractions, using a continuous NaCl gradient of 0.2 to 1 M, over a 25 ml volume. NS5B-containing fractions were identified by sodium dodecyl sulfate polyacrylamide gel electrophoresis (SDS-PAGE), followed by western blotting using the anti-NS5B antiserum at a dilution of 1:2000. Positive fractions were pooled and the elution buffer was exchanged against a 50 mM $NaPO_4$ pH 7.0, 20% glycerol, 0.5% triton X-100 and 10 mM DTT, using a PD-10 column (Amersham-Pharmacia). The sample was then loaded onto a 1 ml HiTrap® SP column (Amersham-Pharmacia), with a flow rate of 0.1 ml/min. Bound proteins were eluted using a continuous 0 to 1 M NaCl gradient over a 15 ml volume. Eluted fractions were analyzed by SDS-PAGE and western blotting. Alternatively, proteins were visualized, following SDS-PAGE, by silver staining using the Silver Stain Plus kit (BioRad) as described by the manufacturer. Positive fractions were tested for RdRp activity (see below) and the most active ones were pooled, and stored as a 40% glycerol solution at −70° C.

In vitro RNA-dependent RNA Polymerase Assays Used to Evaluate Triphosphate Form of Guanosine Analogues RdRp assays were conducted using either homopolymeric template/primers or in vitro transcribed RNA templates.

All RdRp reactions which used homopolymeric template/primers were performed in a total volume of 50 µl of a buffer consisting of 20 mM Tris-HCl pH 7.5, 1 mM DTT, 50 mM NaCl, 0.5 mM $MnCl_2$, 5 µCi [γ $^{32}$P]-GTP (3000 Ci/mmol), and 4 µM of cold GTP. Standard HCV RdRp reactions contained 200 ng of purified NS5SB protein. Guanosine analogues were tested in the presence of polyC/oligoG. PolyC RNAs (Amersham-Pharmacia) was resuspended at 400 ng/µl. The primer $oligoG_{12}$ (MWG, Germany) was diluted to a concentration of 20 pmol/µl (7.6 ng/µl). Templates and primers were mixed volume to volume, denatured at 95° C. for 5 min and annealed at 37° C. for 10 min. Following a two hour incubation at 22° C., reactions were stopped by the addition of 100 µg of sonicated salmon sperm DNA (Life Technologies) and 1 ml of 10% trichloroacetic acid-0.5% tetrasodium pyrophosphate (TCA-PPi). Nucleic acids were precipitated at 4° C. for 30 min after which samples were filtered on GF/C glass microfiber filters (Millipore). Membranes were subsequently washed with 25 ml of a 1% TCA-0.1% PPi solution, then air dried. Incorporated radioactivity was quantified using a liquid scintillation counter (1450-Microbeta, Wallac).

Heteropolymeric RNA templates were generated by run-off transcription. As template for these transcription reactions, a recombinant pcDNA3 plasmid (Invitrogen) containing a cDNA version of the HCV genome was used and referred to as pcDNA/HCVfl. In vitro transcriptions were performed using the MEGAscript™ kit (Ambion), as suggested by the manufacturer. In brief, the plasmid pcDNA/HCVfl was linearized with EcoRI to generate a truncated HCV transcript of about 6900 nucleotides. Linearized DNA was extracted with a one to one volume of phenol/chloroform, precipitated with ethanol, then 1 µg of this linearized DNA was used as template in T7 RNA polymerase-driven in vitro transcription reactions. Transcripts were extracted using the TRIZOL® reagent (Life Technologies) and an aliquot (1 µg) was used as template in RdRp assays. RdRp reactions using heteropolymeric templates were carried out under the same conditions as described above for homopolymeric template/primers, with the exception that the substrate mixture composition consisted of 5 µCi of [γ $^{32}$P]-GTP, 1 µM cold GTP and 100 µM of the remaining nucleotides (ATP, CTP and UTP). Reaction mixtures were subsequently processed as described above for homopolymeric template-containing reactions. Results are shown below:

| Compound | HCV polymerase % inhibition |
|---|---|
| 9(-)-triphosphate | 44%@100 μM |
| 13(-) triphosphate | 82%@50μM |
| | $IC_{50}$ = 10 μM |
| 14(-)-triphosphate | 6%@50μM |

In vitro RNA-dependent RNA Polymerase Assays Used to Evaluate Triphosphate Form of Cytosine Analogues RdRp assays were conducted using either homopolymeric template/primers or in vitro transcribed RNA templates.

All RdRp reactions which used homopolymeric template/primers were performed in a total volume of 50 μl of a buffer consisting of 20 mM Tris-HCl pH 7.5, 1 mM DTT, 50 mM NaCl, 0.5 mM $MnCl_2$, 5 μCi [γ $^{32}$P]-CTP (3000 Ci/mmol), and 5 μM of cold CTP. Standard HCV RdRp reactions contained 200 ng of purified NS5B protein. Cytosine analogues were tested in the presence of polyrI/oligodC. PolyrI RNAs (Amersham-Pharmacia) was resuspended at 400 ng/μl. The primer oligod$C_{12}$ (Life Technologies) was diluted to a concentration of 20 pmol/μl. Templates and primers were mixed volume to volume, denatured at 95° C. for 5 min and annealed at 37° C. for 10 min. Following a two hour incubation at 22° C., reactions were stopped by the addition of 100 μg of sonicated salmon sperm DNA (Life Technologies) and 1 ml of 10% trichloroacetic acid-0.5% tetrasodium pyrophosphate (TCA-PPi). Nucleic acids were precipitated at 4° C. for 30 min after which samples were filtered on GF/C glass microfiber filters (Millipore). Membranes were subsequently washed with 25 ml of a 1% TCA-0.1% PPi solution, then air dried. Incorporated radioactivity was quantified using a liquid scintillation counter (1450-Microbeta, Wallac).

Heteropolymeric RNA templates were generated by run-off transcription. As template for these transcription reactions, a recombinant pcDNA3 plasmid (Invitrogen) containing a cDNA version of the HCV genome was used and referred to as pcDNA/HCVfl. In vitro transcriptions were performed using the MEGAscript™ kit (Ambion), as suggested by the manufacturer. In brief, the plasmid pcDNA/HCVfl was linearized with EcoRI to generate a truncated HCV transcript of about 6900 nucleotides. Linearized DNA was extracted with a one to one volume of phenol/chloroform, precipitated with ethanol, then 1 μg of this linearized DNA was used as template in T7 RNA polymerase-driven in vitro transcription reactions. Transcripts were extracted using the TRIZOL® reagent (Life Technologies) and an aliquot (1 μg) was used as template in RdRp assays.

RdRp reactions using heteropolymeric templates were carried out under the same conditions as described above for homopolymeric template/primers, with the exception that the substrate mixture composition consisted of 5 μCi of [γ $^{32}$P]-CTP, 1 μM cold CTP and 100 μM of the remaining nucleotides (ATP, GTP and UTP). Reaction mixtures were subsequently processed as described above for homopolymeric template-containing reactions. Results are shown below:

| COMPOUND | HCV polymerase % inhibition |
|---|---|
| COMPOUND#22(+) | 85%@50 μM |
| | $IC_{50}$ = 7.7 μM |
| COMPOUND#22(-) | 15%@100 μM |
| COMPOUND#23(+) | 57%@100 μM |
| COMPOUND#23(-) | 81%@100 μM |
| | $IC_{50}$ = 16 μM |
| COMPOUND#24(+) | 12%@50 μM |
| COMPOUND#24(-) | 8%@100 μM |
| COMPOUND#25(+) | 9%@50 μM |
| COMPOUND#26(+) | 47%@100 μM |

EXAMPLE 13

Cytotoxicity Assay

The cytotoxicity of test compounds was evaluated according to the following procedure:

Flat bottom 96 well plates were plated with 5X10E3 Vero-34 cells/well and 1X10E4 Hs-68 or Wi-38 cells/well respectively and incubated overnight at 37° C. and 5% $CO_2$/air. After incubation, the supernatant medium was removed and replaced with test compound dilutions in 2% DMEM (150 μl). The cells were then incubated 48 hours in a 5% $CO_2$ incubator at 37° C.

50 μl/well of 10 μCi/ml solution of [$^3$H]-methyl thymidine (specific activity of approx. 2 Ci/mmol) was added to the culture medium and incubated overnight (18 hours) in a 5% $CO_2$ incubator at 37° C.

Cells were then collected onto a fiberglass filter (Printed Filtermat A 1450-421 Wallac) with a Tomtec cell harvester. Suspended cells were collected directly onto filter while for adherent cells, the medium was first removed, then the cells washed with PBS and trypsinized for 2–3 minutes (50 μl trypsin/well) before collecting.

Filters were dried for 1 hour at 37–40° C. and then placed into bags (1450-microbeta # 1450-432 Wallac) with 4.5 ml of Betascint and counts obtained with Microbeta 1450 Wallac.

The percent of cell proliferation was determined by comparison to the control (no test compound) and thereby establishing 50% inhibitory concentration is established.

We claim:

1. A method for treating a Flaviviridea viral infection in a host comprising administering a therapeutically effective amount of at least one compound having the formula I or a pharmaceutically acceptable salt thereof:

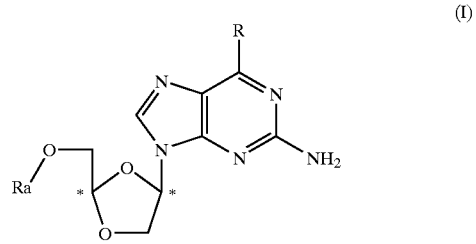

(I)

wherein:

R is H, —$NR_2R_3$ or $OR_4$ wherein $R_2$ is H, $C_{1-6}$ alkyl, $C_{2-6}$ alkenyl, $C_{2-6}$ alkynyl, $C_{3-8}$cycloalkyl;

$R_3$ is H, $C_{1-6}$ alkyl, $C_{2-6}$ alkenyl, $C_{2-6}$ alkynyl;

$R_4$ is H, $C_{1-6}$ alkyl, $C_{2-6}$ alkenyl, $C_{2-6}$ alkynyl; and

Ra is chosen from H, monophosphate, diphosphate, triphosphate, carbonyl substituted with a $C_{1-6}$ alkyl, $C_{2-6}$ alkenyl, $C_{2-6}$ alkynyl, $C_{6-10}$ aryl and

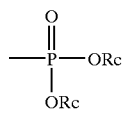

wherein
each Rc is independently chosen from H, $C_{1-6}$ alkyl, $C_{2-6}$ alkenyl, $C_{2-6}$ alkynyl and an hydroxy protecting group;
wherein said nucleoside is present in the form of the (−) enantiomer, (+) enantiomer and mixtures thereof, including racemic mixtures.

2. The method of claim 1 wherein R is $NH_2$, H or OH.
3. The method of claim 1 wherein R is $NH_2$ or OH.
4. The method of claim 1 wherein R is OH.
5. The method of claim 1 wherein R is $—NR_2R_3$ wherein $R_2$ is cycloropyl and $R_3$ is H.
6. The method of claim 1 wherein Ra is chosen from H, monophosphate, diphosphate, and triphosphate.
7. The method of claim 1 wherein Ra is chosen from monophosphate, diphosphate, and triphosphate.
8. The method of claim 1 wherein Ra is triphosphate.
9. The method of claim 1 wherein Ra is H.
10. The method as defined in claim 1 wherein said compound of formula I of the present invention is substantially in the form of the (−) enantiomer.
11. The method of claim 1 which comprises administering at least one compound chosen from:

Compound 1  cis-2-hydroxymethyl-4-(2'-amino-6'-cyclopropylamino-purine-9'-yl)-1,3-dioxolane;
Compound 2  cis-2-hydroxymethyl-4-(2'-amino-6'-cyclobutylamino-purine-9'-yl)-1,3-dioxolane;
Compound 3  cis-2-hydroxymethyl-4-(2'-amino-6'-cyclopentylamino-purine-9'-yl)-1,3-dioxolane;
Compound 4-cis-2-hydroxymethyl-4-(2'-6'-diamino-purin-9'-yl)-1,3-dioxolane;
Compound 5  cis-2-hydroxymethyl-4-(guanin-9'-yl)-1,3-dioxolane;
Compound 6  cis-2-hydroxymethyl-4-(adenin-9'-yl)-1,3-dioxolane;
Compound 7  cis-2-hydroxymethyl-4-(2'amino-6'-chloro-purin-9'-yl)-1,3-dioxolane; or
Compound 8  cis-2-hydroxymethyl-4-(2'amino-purin-9'-yl)-1,3-dioxolane.

12. The method of claim 1 which comprises administering at least one compound chosen from Compound 1(−) cis-2-hydroxymethyl-4-(2'-amino-6'-cyclopropylamino-purine-9'-yl)-1,3-dioxolane;
Compound 2(−) cis-2-hydroxymethyl-4-(2'-amino-6'-cyclobutylamino-purine-9'-yl)-1,3-dioxolane;
Compound 3(−) cis-2-hydroxymethyl-4-(2'-amino-6'-cyclopentylamino-purine-9'-yl)-1,3-dioxolane;
Compound 4(−) -cis-2-hydroxymethyl-4-(2'-6'-diamino-purin-9'-yl)-1,3-dioxolane;
Compound 5(−) cis-2-hydroxymethyl-4-(guanin-9'-yl)-1,3-dioxolane;
Compound 6)(−) cis-2-hydroxymethyl-4-(adenin-9'-yl)-1,3-dioxolane;
Compound 7(−) cis-2-hydroxymethyl-4-(2'amino-6'-chloro-purin-9'-yl)-1,3-dioxolane; or
Compound 8(−) cis-2-hydroxymethyl-4-(2'amino-purin-9'-yl)-1,3-dioxolane.

13. The method as defined in claim 1 wherein said Flaviviridae viral infection is hepatitis C.
14. The method as defined in claim 10 wherein said Flaviviridae viral infection is hepatitis C.
15. The method as defined in claim 11 wherein said Flaviviridae viral infection is hepatitis C.
16. The method as defined in claim 12 wherein said Flaviviridae viral infection is hepatitis C.
17. A method for treating a Flaviviridae viral infection in a host comprising administering a therapeutically effective amount of at least one compound having the formula II or a pharmaceutically acceptable salt thereof:

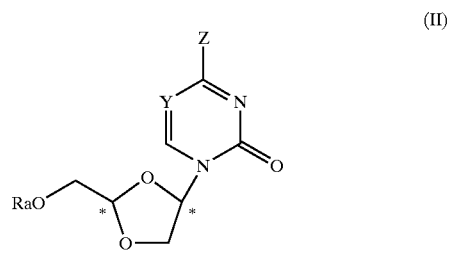

(II)

wherein
Z is H, $—NR'_2R_3$, or $OR_{4'}$ wherein
$R_{2'}$ is H, $C_{1-6}$ alkyl, $C_{2-6}$ alkenyl, or $C_{2-6}$ alkynyl;
$R_{3'}$ is H or a $C_{1-6}$ alkyl, $C_{2-6}$ alkenyl, $C_{2-6}$ alkynyl;
$R_{4'}$ is H, $C_{1-6}$ alkyl, $C_{2-6}$ alkenyl, $C_{2-6}$ alkynyl, and
Y is N or C—X;
X is chosen from of H, halogen, $C_{1-6}$ alkyl, $C_{2-6}$ alkenyl, $C_{2-6}$ alkynyl, CN, $CF_3$, $N_3$, $NO_2$, $C_{6-10}$ aryl, $C_{6-10}$ heteroaryl and CORb wherein Rb is chosen from of H, OH, SH, $C_{1-6}$ alkyl, $C_{1-6}$ aminoalkyl, $C_{1-6}$ alkoxy and $C_{1-6}$ thioalkyl;
and Ra is chosen from of H, monophosphate, diphosphate, triphosphate, carbonyl subsunited with a $C_{1-6}$ alkyl, $C_{2-6}$ alkenyl, $C_{2-6}$ alkynyl, $C_{6-10}$ aryl, and

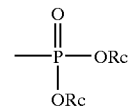

wherein
each Rc are independently chosen from H, $C_{1-6}$ alkyl, $C_{2-6}$ alkenyl, $C_{2-6}$ alkynyl and an hydroxy protecting group,
wherein said compounds is in the form of a single enantiomer or a mixture thereof including racemic mixtures.

18. The method of claim 17 wherein said compound of formula II of the present invention is substantially in the form of the (+) enantiomer.
19. The method of claim 17 wherein sais compound of formula II of the present invention is substantially in the form of the (−) enatiomer.
20. The method of claim 17 wherein Ra is chosen from H, monophosphate, diphosphate, and triphosphate.
21. The method of claim 17 wherein Ra is chosen from monophosphate, diphosphate, and triphosphate.
22. The method of claim 17 wherein Ra is triphosphate.
23. The method of claim 17 wherein Ra is H.
24. The method of claim 17 wherein Y is C—X.
25. The method of claim 17 wherein Y is C—X and X is H, methyl, or Halogen.

26. The method of claim 17 wherein Y is C—X and X is H, methyl or halogen.
27. The method of claim 17 wherein Y is C—X and X is H, methyl or F.
28. The method of claim 17 wherein Y is C—X and X is H or F.
29. The method of claim 17 wherein Y is C—X and X is H.
30. The method of claim 17 wherein Y is C—X and X is F.
31. The method of claim 17 wherein Z is OH.
32. The method of claim 17 wherein Z is $NH_2$.
33. The method of claim 18 wherein Ra is chosen from H, monophosphate, diphosphate, and triphosphate.
34. The method of claim 18 wherein Ra is chosen from monophosphate, diphosphate, and triphosphate.
35. The method of claim 18 wherein Ra is triphosphate.
36. The method of claim 18 wherein Ra is H.
37. The method of claim 18 wherein Y is C—X.
38. The method of claim 18 wherein Y is C—X and X is H, methyl, or Halogen.
39. The method of claim 18 wherein Y is C—X and X is H, methyl or halogen.
40. The method of claim 18 wherein Y is C—X and X is H, methyl or F.
41. The method of claim 18 wherein Y is C—X and X is H or F.
42. The method of claim 18 wherein Y is C—X and X is H.
43. The method of claim 18 wherein Y is C—X and X is F.
44. The method of claim 18 wherein Z is OH.
45. The method of claim 18 wherein Z is $NH_2$.
46. The method of claim 19 wherein Ra is chosen from H, monophosphate, diphosphate, and triphosphate.
47. The method of claim 19 wherein Ra is chosen from monophosphate, diphosphate, and triphosphate.
48. The method of claim 19 wherein Ra is triphosphate.
49. The method of claim 19 wherein Ra is H.
50. The method of claim 19 wherein Y is C—X.
51. The method of claim 19 wherein Y is C—X and X is H, methyl, or Halogen.
52. The method of claim 19 wherein Y is C—X and X is H, methyl or halogen.
53. The method of claim 19 wherein Y is C—X and X is H, methyl or F.
54. The method of claim 19 wherein Y is C—X and X is H or F.
55. The method of claim 19 wherein Y is C—X and X is H.
56. The method of claim 19 wherein Y is C—X and X is F.
57. The method of claim 19 wherein Z is OH.
58. The method of claim 19 wherein Z is $NH_2$.
59. The method of claim 17 wherein the compound of formula II is (+)Cis-2-hydroxymethyl-4-(cytosin-1'-yl)-1,3-Dioxolane.
60. The method of claim 17 wherein the compound of formula II is (+)Cis-2-hydroxymethyl-4-(5'-fluorocytosin-1'-yl)-1,3-Dioxolane.
61. The method of claim 17 wherein the compound of formula II is (−)Cis-2-hydroxymethyl-4-(5'-fluorocytosin-1'-yl)-1,3-Dioxolane.
62. The method of claim 17 wherein the compound of formula II is (+)Cis-2-hydroxymethyl-4-(5'-azacytosin-1'-yl)-1,3-Dioxolane.
63. The method of claim 17 wherein the compound of formula II is (+)-cis-2-hydroxymethyl-4-(5'-methylcytosin-1'-yl)-1,3-dioxolane (β-D-).
64. The method of claim 17 wherein the compound of formula II is (+)-cis-2-hydroxymethyl-4-(N-1'-thiminyl)-1,3-dioxolane (-D-).
65. The method of claim 17 wherein said Flaviviridea viral infection is hepatitis C.
66. A method for treating a Flaviviridae viral infection in a host comprising administering a therapeutically effective amount of at least one compound of formula I or II, or a pharmaceutically acceptable salt thereof:

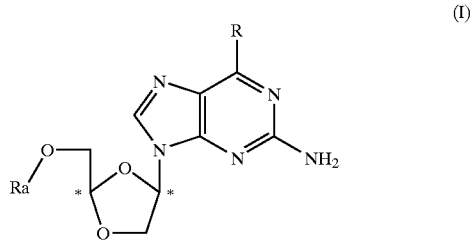
(I)

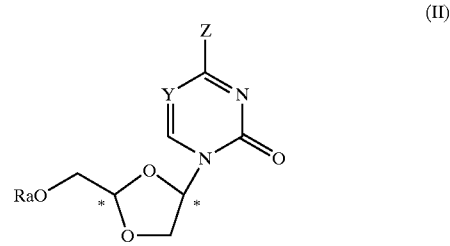
(II)

wherein

R is H, —$NR_2R_3$ or $OR_4$, $R_2$ is H, $C_{1-6}$ alkyl, $C_{2-6}$ alkenyl, $C_{2-6}$ alkynyl, $C_{3-8}$ cycloalkly;

$R_3$ is H, $C_{1-6}$ alkyl, $C_{2-6}$ alkenyl, $C_{2-6}$ alkynyl, $R_4$ is H, $C_{1-6}$ alkyl, $C_{2-6}$ alkenyl, $C_{2-6}$ alkynyl, and Ra is chosen from H, monophosphate, diphosphate, triphosphate, carbonyl substituted with a $C_{1-6}$ alkyl, $C_{2-6}$ alkenyl, $C_{2-6}$ alkynyl, $C_{6-10}$ aryl and

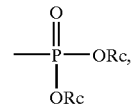

Rc, in each case, is independently chosen from H, $C_{1-6}$ alkyl, $C_{2-6}$ alkenyl, $C_{2-6}$ alkynyl and an hydroxy protecting group;

Z is H, —$NR_2R_3$, or $OR_4$, $R_{2'}$, is H, $C_{1-6}$ alkyl, $C_{2-6}$ alkenyl, or $C_{2-6}$ alkynyl;

$R_{3'}$, is H or a $C_{1-6}$ alkyl, $C_{2-6}$ alkenyl, $C_{2-6}$ alkynyl;

$R_{4'}$, is H, $C_{1-6}$ alkyl, $C_{2-6}$ alkenyl, $C_{2-6}$ alkynyl; and

Y is N or C—X;

X is chosen from of H, halogen, $C_{1-6}$ alkyl, $C_{2-6}$ alkenyl, $C_{2-6}$ alkynyl, CN, $CF_3$, $N_3$, $NO_2$, $C_{6-10}$ aryl, $C_{6-10}$ heteroaryl and CORb, and Rb is chosen from of H, OH, SH, $C_{1-6}$ alkyl, $C_{1-6}$ aminoalkyl, $C_{1-6}$ alkoxy and $C_{1-6}$ thioalkyl.

* * * * *

UNITED STATES PATENT AND TRADEMARK OFFICE
CERTIFICATE OF CORRECTION

PATENT NO. : 6,566,365 B1
DATED : May 20, 2003
INVENTOR(S) : Richard Storer

It is certified that error appears in the above-identified patent and that said Letters Patent is hereby corrected as shown below:

Title page,
Item [54], should read, "FLAVIVIRIDEA" should read -- FLAVIVIRIDAE --

Column 40,
Line 46, reads "Flaviviridea" should read -- Flaviviridae --

Column 41,
Line 39, reads "Compound 4-cis" should read --Compound 4 cis --
Line 58, reads "-cis" should read -- cis --
Line 62, reads "6)" should read -- 6 --

Column 42,
Line 26, reads "--$NR_2R_3$" should read -- $NR_{2'}R_{3'}$ --
Lines 32, 34 and 37, reads "from of H," should read -- from H, --
Line 38, reads "subsunited" should read -- substituted --
Line 48, reads "Rc are" should read -- Rc is --
Line 51, reads "said compounds" should read -- said compound --
Line 56, reads "sais compound" should read -- said compound --
Line 58, reads "enatiomer." should read -- enantiomer. --

Column 44,
Line 7, reads "Flaviviridea" should read -- Flaviviridae --
Line 38, reads "cycloalkly;" should read -- cycloalkyl; --
Line 55, reads "$R_{2'}$," should read -- $R_{2'}$ --
Line 56, reads "$R_{3'}$," should read -- $R_{3'}$ --
Line 57, reads "$R_{4'}$," should read -- $R_{4'}$ --
Lines 59 and 62, reads, "from of H," should read -- from H, --

Signed and Sealed this

Fourteenth Day of September, 2004

JON W. DUDAS
*Director of the United States Patent and Trademark Office*